United States Patent
Tian et al.

(10) Patent No.: US 11,926,675 B2
(45) Date of Patent: *Mar. 12, 2024

(54) ANTIBODIES BINDING CD24, PREPARATION AND USE THEREOF

(71) Applicant: ImmuneOnco Biopharmaceuticals (Shanghai) Inc., Shanghai (CN)

(72) Inventors: Wenzhi Tian, Shanghai (CN); Song Li, Shanghai (CN); Dianze Chen, Shanghai (CN); Huiqin Guo, Shanghai (CN)

(73) Assignee: IMMUNEONCO BIOPHARMACEUTICALS (SHANGHAI) INC., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/685,530

(22) Filed: Mar. 3, 2022

(65) Prior Publication Data

US 2023/0110607 A1  Apr. 13, 2023

(30) Foreign Application Priority Data

Oct. 13, 2021 (CN) .......................... 202111195246.5

(51) Int. Cl.
*C07K 16/28* (2006.01)
*A61P 35/00* (2006.01)
(Continued)

(52) U.S. Cl.
CPC .......... *C07K 16/2896* (2013.01); *A61P 35/00* (2018.01); *A61K 2039/505* (2013.01);
(Continued)

(58) Field of Classification Search
CPC ............ C07K 16/2896; C07K 2317/24; C07K 2317/732; C07K 2317/92; A61P 35/00; A61K 2039/505
See application file for complete search history.

(56) References Cited

U.S. PATENT DOCUMENTS

2023/0114491 A1*  4/2023  Tian .................. A61P 35/02
424/133.1

FOREIGN PATENT DOCUMENTS

| CN | 103819561 A | 5/2014 |
|----|-------------|--------|
| CN | 106589126 A | 4/2017 |

(Continued)

OTHER PUBLICATIONS

Kristiansen et al., Molecular and clinical dissection of CD24 antibody specificity by a comprehensive comparative analysis, Laboratory Investigation (2010); vol. 90; pp. 1102-1116.) (Year: 2010).*

(Continued)

*Primary Examiner* — Aurora M Fontainhas
*Assistant Examiner* — Selam Berhane
(74) *Attorney, Agent, or Firm* — Duane Morris LLP; Thomas J. Kowalski; Deborah L. Lu

(57) ABSTRACT

Disclosed is an antibody that specifically binds CD24, or an antigen binding portion thereof. A nucleic acid molecule encoding the antibody or antigen binding portion thereof, an expression vector and a host cell comprising the nucleic acid molecule, a method for expressing the antibody or antigen binding portion thereof, and a method for treating a disease associated with CD24 signaling using the antibody or antigen binding portion thereof are also provided.

14 Claims, 7 Drawing Sheets

Specification includes a Sequence Listing.

IMM47    IMM47C    IMM47H

(51) Int. Cl.
*A61P 35/02* (2006.01)
*A61K 39/00* (2006.01)

(52) U.S. Cl.
CPC .... *C07K 2317/24* (2013.01); *C07K 2317/732* (2013.01); *C07K 2317/92* (2013.01)

(56) References Cited

FOREIGN PATENT DOCUMENTS

| CN | 108373504 A | 8/2018 |
|---|---|---|
| CN | 113831412 A | 12/2021 |
| WO | 2019222082 A1 | 11/2019 |
| WO | 2019241403 A1 | 12/2019 |
| WO | 2020261280 A1 | 12/2020 |

OTHER PUBLICATIONS

Sagiv et al, Targeting CD24 for Treatment of Colorectal and Pancreatic Cancer by Monoclonal Antibodies or Small Interfering RNA, 2008, Cancer Res: 68(8), pp. 2803-2812. (Year: 2008).*

EPO, European search report of EP22156295.2, the counterpart application filed with EPO, dated Aug. 1, 2022.
Sun Fumou et al: "Engineering a high-affinity humanized anti-CD24 antibody to target hepatocellular carcinoma by a novel CDR grafting design", ONCOTARGET, vol. 8, No. 31, Aug. 1, 2017, pp. 51238-51252.
ISA/CN, International Search Report & Written Opinion of the International Searching Authority of corresponding application PCT/CN2022/114945, dated Nov. 28, 2022.
Salnikov,A.V. et al., Antibody targeting of CD24 efficiently retards growth and influences cytokine milieu in experimental carcinomas, British Journal of Cancer, Mar. 19, 2013(Mar. 19, 2013) vol. 108,pp. 1449-1459.
Sun, F. et al., Anti-CD24 Antibody-Nitric Oxide Conjugate Selectively and Potently Suppresses Hepatic Carcinoma, Cancer Research, Jul. 1, 2019(Jul. 1, 2019) vol. 79, No. 13, pp. 3395-3405.
Wu, H. et al., Prospects of antibodies targeting CD47 or CD24 in the treatment of glioblastoma, CNS Neuroscience & Therapeutics, Aug. 6, 2021(Aug. 6, 2021) vol. 27,pp. 1105-1117.
JPO Non-Final Office Action of counterpart application JP2022-019864, dated Mar. 22, 2023.

* cited by examiner

ANTIBODIES BINDING CD24, PREPARATION AND USE THEREOF

RELATED APPLICATIONS AND INCORPORATION BY REFERENCE

This application claims priority to Chinese Patent Application No. 202111195246.5 filed on Oct. 13, 2021.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing which has been submitted electronically and is hereby incorporated by reference in its entirety. Said ASCII copy was created Feb. 6, 2022 and revised Mar. 9, 2022, is named 55525_00062SubstituteSL.txt and is 24,117 bytes in size.

FIELD OF THE INVENTION

The application relates to a monoclonal antibody or an antigen binding portion thereof that specifically binds CD24, and the preparation and use thereof, especially the use in tumor therapies.

BACKGROUND OF THE INVENTION

Cancer cells have developed several mechanisms to evade hosts' immune surveillance, including: 1) to highly express CD24 proteins, which may bind Siglecs on immune cells, to inhibit antitumor immune responses; 2) to promote detachment of MICA/MICB from cancer cell membranes, which bind to NKG2D proteins on natural killer (NK) cell surfaces, blocking MICA/MICB$^+$ cancer cell killing by NK cells; and 3) to express a high level of CD47s, which bind to the signal regulatory protein alpha (SIRPα) on macrophage surfaces, inducing inhibitory signals that inhibit phagocytosis of cancer cells by macrophages. It can be seen that the cancer cells are quite "smart" and reproduce quickly depending on their developed evasion mechanisms. Accordingly, development of effective anti-cancer drugs for killing the cancer cells may focus on targeting these mechanisms.

CD24

CD24 is a glycosyl-phosphatidylinositol-anchored protein on many cells of the immune system. It functions as a costimulatory molecule for T cells and a regulator of autoimmunity. CD24 is also highly expressed in various cancer cells including the cells of ovarian cancer, breast cancer, cervical cancer, endometrial cancer, acute lymphoblastic leukemia (ALL), cholangiocarcinoma, bladder cancer, pancreatic cancer, stomach adenocarcinoma, and glioblastoma (Barkal et al., 2019; Liu et al., 2013), and regulates migration, invasion and proliferation of cancer cells.

CD24 is a ligand for P-selectin, a transmembrane protein that functions as a cell adhesion molecule on the surfaces of activated endothelial cells and activated platelets. The CD24-P-selectin interaction may enhance tumor metastasis (Friederichs J et al., 2000). CD24 also binds Siglects, the sialic acid binding receptors that are expressed on immune cells, among which Siglec-5 and Siglec-10 are important inhibitory receptors on monocytes, granulocytes and lymphocytes. Siglec-10 expression on T cells is known to interfere with T cell activation by inhibiting the formation of T cell major histocompatibility complex class I (MHC-I) peptide complex and phosphorylation of T cell receptor-associated kinase, Lck, and ZAP-70 (Yin, et al., 2020). Siglec-10 expression on B cells and NK cells can inhibit BCR-mediated and NK cell receptor-mediated signal transduction, respectively (Yin, et al., 2020). Tumor cells may make use of CD24s to produce a 'don't eat me' signal with Siglec-10, so as to shield them from immune attacks.

Accordingly, CD24 is deemed as a biomarker of poor prognosis. CD24 expression is significantly associated with bladder tumor recurrence (Liu et al., 2013). In patients with ovarian cancer, expression of CD24 was found to correlate with tumor staging and peritoneal and lymph node metastasis. Further, CD24-positive cells showed enhanced proliferation, a highly invasive phenotype, and were reported to be associated with cisplatin resistance in ovarian cancer cells (Nakamura et al. 2017).

Studies have shown anti-CD24 monoclonal antibodies can reduce lung metastasis and prolong the overall survival in bladder cancer and triple-negative breast cancer mouse models. Literature also revealed that antibody blockade of CD24-Siglec-10 interaction resulted in a macrophage-dependent reduction of tumor growth and extension of survival in tumor-bearing mice (Barkal, et al., 2019; Chan et al., 2019; Overdevest et al., 2011). In addition, previous studies demonstrated that anti-CD47/CD24 dual antibody treatment could effectively activate the myeloid immunity in the brain (Wu H, et al, 2021). And such dual treatment was revealed to augment phagocytosis against human ovarian cancer cells (Barkal et al., 2019). Barakal et al also found that compared to the either treatment alone, combination treatment of CD24 antibody and cetuximab (Erbitux) further enhanced phagocytosis of pancreatic adenocarcinoma cells.

CD24 upregulation may be also involved in graft versus host disease (GVHD) (Toubai, T., et al., 2014), metabolic associated fatty liver disease (Fairbridge, N. A., et al., 2015), Type 1 diabetes mellitus (El-Mokhtar, M. A., et al., 2020), multiple sclerosis, rheumatoid arthritis, systemic lupus erythematosus (Tan, Y., et al., 2016), and sepsis (Chen, G. Y., et al., 2011) (References 7 to 15).

More anti-CD24 antibodies with superior characteristics are needed.

Citation or identification of any document in this application is not an admission that such a document is available as prior art to the present disclosure.

SUMMARY OF THE INVENTION

The present application discloses a novel anti-CD24 antibody or an antigen binding portion thereof, which may bind CD24$^+$ cells, and induce antibody dependent cell mediated cytotoxicity (ADCC) against CD24$^+$ cells. The antibody or antigen binding portion thereof of the disclosure also showed potent in vivo anti-tumor effects. Particularly, the administration of the anti-CD24 antibody or antigen binding portion thereof of the disclosure at certain doses may completely eliminate the tumors in animals, and re-transplantation of tumor cells will not lead to tumor formation or growth in these animals even though they are no longer given the antibody or antigen binding portion thereof.

Specifically, in an aspect, the present application discloses an isolated monoclonal antibody or an antigen binding portion thereof, that binds CD24, that may comprise i) a heavy chain variable region that may comprise a heavy chain variable region CDR1 (VH-CDR1), a VH-CDR2 and a VH-CDR3, wherein the VH-CDR1, the VH-CDR2 and the VH-CDR3 may comprise amino acid sequences having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 1, 2 and 3, respectively; and/or ii) a light chain variable region that may comprise a light chain variable region CDR1 (VL-CDR1), a VL-CDR2 and a VL-CDR3, wherein the VL-CDR1, the VL-CDR2 and the VL-CDR3 may comprise amino acid sequences having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 4, 5 and 6, respectively.

The heavy chain variable region of the disclosure may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 7 or 10.

The light chain variable region of the disclosure may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NOs: 8, 9 or 11.

The isolated monoclonal antibody or antigen-binding portion thereof of the disclosure may comprise a heavy chain variable region and a light chain variable region which may comprise amino acid sequences having at least 80%, 81%, 82%, 83%, 84%, 85%, 86%, 87%, 88%, 89%, 90%, 91%, 92%, 93%, 94%, 95%, 96%, 97%, 98%, 99% or 100% identity to (1) SEQ ID NOs: 7 and 8, respectively; (2) SEQ ID NOs: 7 and 9, respectively; or (3) SEQ ID NOs: 10 and 11, respectively.

The isolated monoclonal antibody or antigen binding portion thereof of the disclosure may comprise a heavy chain constant region and/or a light chain constant region. The heavy chain constant region may be an IgG1, IgG2, IgG3 or IgG4 heavy chain constant region, or a functional fragment thereof, that has or has been engineered to have FcR and/or complement system protein (such as C1q) binding affinity. In certain embodiments, the heavy chain constant region may be human IgG1 heavy chain constant region, comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to e.g., SEQ ID NO: 12. The light chain constant region may be kappa light chain constant region, such as human kappa light chain constant region, comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% identity to e.g., SEQ ID NO: 13. The N terminus of the heavy chain constant region is linked to the C terminus of the heavy chain variable region, and the N terminus of the light chain constant region is linked to the C terminus of the light chain variable region.

In certain embodiments, the antibody of the disclosure may be an IgG antibody, comprising or consisting of two heavy chains and two light chains connected by disulfide bonds, wherein each heavy chain may comprise the heavy chain constant region, heavy chain variable region and/or CDR sequences mentioned above, and each light chain may comprise the light chain constant region, light chain variable region and/or CDR sequences mentioned above.

The antibody or antigen binding portion thereof of the disclosure may be mouse, chimeric, human or humanized.

The antibody or antigen binding portion thereof of the disclosure may bind CD24, block the binding of CD24 to e.g., Siglec-10, induce ADCC against CD24$^+$ cells, and show potent in vivo anti-tumor effects.

The disclosure also provides an immuneconjugate comprising the antibody or the antigen binding portion thereof, linked to a therapeutic agent such as a cytotoxin or an anti-cancer agent. The disclosure also provides a bispecific molecule comprising the antibody or the antigen-binding portion thereof of the disclosure, linked to a second functional moiety (e.g., a second antibody) having a different binding specificity than the antibody or the antigen-binding portion thereof of the disclosure. In another aspect, the antibody or the antigen-binding portion thereof of the present disclosure can be made into part of a chimeric antigen receptor (CAR) or a T cell receptor (TCR). The disclosure further provides an immune cell with the CAR or TCR of the disclosure, such as a T cell and a NK cell.

The disclosure further provides a nucleic acid molecule encoding the antibody or antigen-binding portion thereof of the disclosure, as well as an expression vector comprising such a nucleic acid molecule and a host cell comprising such an expression vector. A method for preparing the anti-CD24 antibody or antigen binding portion thereof using the host cell of the disclosure is provided, comprising the steps of (i) expressing the antibody or antigen binding portion thereof in the host cell, and (ii) isolating the antibody or antigen binding portion thereof from the host cell or its cell culture.

The disclosure provides a pharmaceutical composition comprising the antibody or antigen binding portion thereof, the immuneconjugate, the bispecific molecule, the immune cell, the nucleic acid molecule, the expression vector, or the host cell of the disclosure, and a pharmaceutically acceptable carrier. The pharmaceutical composition of the disclosure may further comprise an anti-tumor agent such as a SIRPalphaD1-Fc fusion protein, or an anti-inflammatory agent.

In another aspect, the disclosure provides a method for treating or alleviating a disease associated with CD24 (e.g., CD24 overexpression or signaling) in a subject in need thereof, comprising administering to the subject a therapeutically effective amount of the pharmaceutical composition of the disclosure.

The disease may be a cancer. The cancer may be a solid cancer or a hematological cancer, including, but not limited to, ovarian cancer, breast cancer, cervical cancer, endometrial cancer, acute lymphoblastic leukemia (ALL), pancreatic adenocarcinoma, cholangiocarcinoma, bladder cancer, pancreatic cancer, gastric adenocarcinoma, glioblastoma, and colon cancer. In certain embodiments, the pharmaceutical composition of the disclosure may be administered with at least one anti-tumor agent, such a protein targeting CD47. The protein targeting CD47 may be a SIRPalphaD1-Fc fusion protein having at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO.: 19, the amino acid sequence of SEQ ID NO: 19 may be encoded by a nucleotide sequence of SEQ ID NO: 20. It contains an N→A mutation at position 80 of SEQ ID NO: 19 to remove a glycosylation site.

In certain embodiments, the disease may be an inflammatory disease, including, but not limited to, acute graft versus host disease, rheumatoid arthritis, and systemic lupus erythematosus.

The disease further includes, but not limited to, metabolic associated fatty liver disease, diabetes mellitus, multiple sclerosis, and sepsis.

The antibody or antigen binding portion thereof of the disclosure may also be used for in vitro detection of CD24 proteins.

Other features and advantages of the instant disclosure will be apparent from the following detailed description and examples which should not be construed as limiting. The contents of all references, GenBank entries, patents and published patent applications cited throughout this application are expressly incorporated herein by reference.

Accordingly, it is an object of the application not to encompass within the application any previously known product, process of making the product, or method of using the product such that Applicants reserve the right and hereby disclose a disclaimer of any previously known product, process, or method. It is further noted that the application does not intend to encompass within the scope of the application any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the application to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the application.

DESCRIPTION OF THE DRAWINGS

The following detailed description, given by way of example, but not intended to limit the application solely to the specific embodiments described, may best be understood in conjunction with the accompanying drawings.

DETAILED DESCRIPTION OF THE APPLICATION

Figure 1:
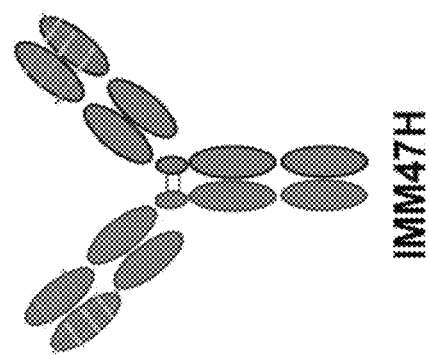
FIG. 1 is a schematic diagram of structures of the anti-CD24 antibodies of the disclosure, IMM47C, IMM47 and IMM47H. IMM47C is an IgG antibody, comprising a mouse heavy chain variable region, a heavy chain constant region, a mouse light chain variable region and a light chain constant region, respectively having the amino acid sequences set forth in SEQ ID NOs: 7, 12, 8 and 13. IMM47 is an IgG antibody, comprising a mouse heavy chain variable region, a heavy chain constant region, a humanized light chain variable region and a light chain constant region, respectively having the amino acid sequences set forth in SEQ ID NOs: 7, 12, 9 and 13. IMM47H is an IgG antibody, comprising a humanized heavy chain variable region, a heavy chain constant region, a humanized light chain variable region and a light chain constant region, respectively having the amino acid sequences set forth in SEQ ID NOs: 10, 12, 11 and 13.
Figure 1:
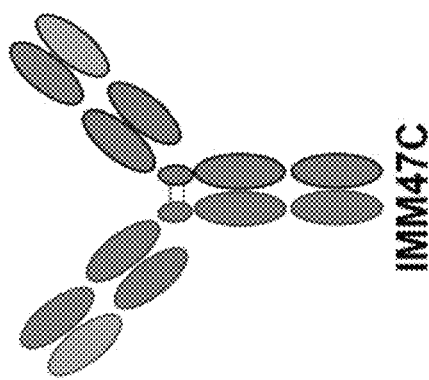
Figure 1:
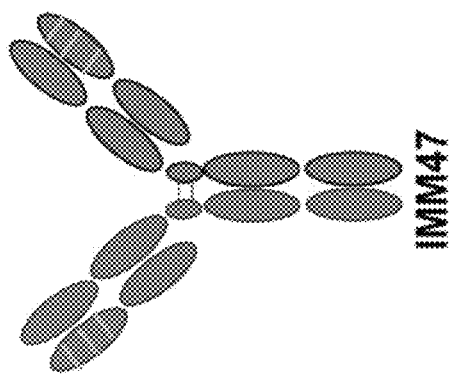

To ensure that the present disclosure may be more readily understood, certain terms are first defined. Additional definitions are set forth throughout the detailed description.

The term "CD24" refers to cluster of differentiation 24. The term "CD24" comprises variants, isoforms, homologs, orthologs and paralogs.

The term "antibody" as referred to herein includes whole antibodies of e.g., IgG, IgA, IgD, IgE and IgM, and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region ($C_H$). The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. A "functional fragment" of a heavy chain constant region refers to a part of the constant region that retains the capability to mediate binding of the immunoglobulin to host tissues or factors, including various cells of the immune system (e.g., effector cells) and the first component (C1q) of the classical complement system, to initiate e.g., ADCC, CDC, ADCP and the like.

The term "antigen-binding portion" of an antibody (or simply "antibody portion"), as used herein, refers to one or more fragments of an antibody that retain the ability to specifically bind to an antigen (e.g., a CD24 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment which may comprise two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a CD24 protein is substantially free of antibodies that specifically bind antigens other than CD24 proteins). An isolated antibody that specifically binds a human CD24 protein may, however, have cross-reactivity to other antigens, such as CD24 proteins from other species. Moreover, an isolated antibody can be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The heavy chain variable region CDRs and the light chain variable region CDRs in the antibody or antigen binding portion thereof of the disclosure have been defined by the IMGT numbering system. However, as is well known in the art, CDR regions can also be determined by other systems such as Chothia, Kabat, AbM, or Contact numbering system/method, based on heavy chain/light chain variable region sequences.

The term "antibody dependent cellular cytotoxicity", "antibody dependent cell-mediated cytotoxicity" or "ADCC" refers to a mechanism of cell-mediated immune defense whereby an effector cell of the immune system actively lyses a target cell bound by e.g., the anti-CD24 antibodies.

The term "$EC_{50}$", also known as half maximal effective concentration, refers to the concentration of an antibody or an antigen binding portion thereof which induces a response halfway between the baseline and maximum after a specified exposure time.

The term "$IC_{50}$", also known as half maximal inhibitory concentration, refers to the concentration of an antibody or an antigen binding portion thereof which inhibits a specific biological or biochemical function by 50% relative to the absence of the antibody or antigen binding portion thereof.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using the publicly available computer software such as ClustalOmega, T-coffee, Kalign and MAFFT. When using such softwares, the default parameters, e.g. for gap penalty and extension penalty, are preferably used.

The term "therapeutically effective amount" means an amount of the antibody or antigen-binding portion thereof of the present disclosure sufficient to prevent or ameliorate the symptoms associated with a disease or condition (such as an inflammatory disease) and/or lessen the severity of the disease or condition. A therapeutically effective amount is understood to be in context to the condition being treated, where the actual effective amount is readily discerned by those of skill in the art.

In an embodiment, an antibody of the disclosure comprises a heavy and/or light chain variable region sequences of CDR1, CDR2 and CDR3 sequences which differ from those of the anti-CD24 antibodies of the present disclosure by one or more conservative modifications. It is understood in the art that certain conservative sequence modification can be made which do not remove antigen binding.

As used herein, the term "conservative sequence modifications" is intended to refer to amino acid modifications that do not significantly affect or alter the binding characteristics of the antibody or antigen binding portion thereof containing the amino acid sequence. Such conservative modifications include amino acid substitutions, additions and deletions. Modifications can be introduced into an antibody or an antigen binding portion thereof of the disclosure by standard techniques known in the art, such as site-directed mutagenesis and PCR-mediated mutagenesis. Conservative amino acid substitutions are ones in which the amino acid residue is replaced with an amino acid residue having a similar side chain Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody or an antigen binding portion thereof of the disclosure can be replaced with other amino acid residues from the same side chain family and the altered antibody can be tested for retained function (i.e., the functions set forth above) using the functional assays described herein.

Antibodies of the disclosure can be prepared using an antibody having one or more of the $V_H/V_L$ sequences of the anti-CD24 antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody or an antigen binding portion thereof can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties.

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences. Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase). As another example, the germline DNA sequences for human heavy and light chain variable region genes can be found in the Genbank database. Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody.

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "back-mutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region between the $C_{H1}$ and $C_{H2}$ regions is modified in such that the number of cysteine residues in the hinge region is altered, e.g., increased or decreased. The number of cysteine residues in the hinge region is altered to, for example, facilitate assembly of the light and heavy chains or to increase or decrease the stability of the antibody.

In another embodiment, the Fc hinge region of an antibody is mutated to increase or decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation.

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art.

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibodies of the disclosure can be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val, Ala-Asn-Val, Val-Leu-Lys, Ala-Ala-Asn, Cit-Cit, Val-Lys, Lys, Cit, Ser, or Glu.

In another aspect, the present disclosure features bispecific molecules comprising one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities. In an embodiment, a bispecific molecule has, in addition to an anti-Fc binding specificity and an anti-CD24 binding specificity, a third specificity. The third specificity can be for CD47, to more accurately target tumor cells while releasing other CD24$^+$ cells such as CD24$^+$ immune cells.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv)$_2$ construct. Intermediate-sized bispecific molecules include two different F(ab) fragments linked by a peptidyl linker. Bispecific molecules of these and other formats can be prepared by genetic engineering, somatic hybridization, or chemical methods.

Also provided herein are a chimeric antigen receptor (CAR) containing an anti-CD24 scFv, the anti-CD24 scFv comprising CDRs and heavy/light chain variable regions described herein.

The anti-CD24 CAR may comprise (a) an extracellular antigen binding domain comprising an anti-CD24 scFv; (b) a transmembrane domain; and (c) an intracellular signaling domain.

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the anti-CD24 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, such that the $V_H$ and $V_L$ sequences can be expressed as a contiguous single-chain protein, with the $V_L$ and $V_H$ regions joined by the flexible linker.

In another aspect, the present disclosure provides a pharmaceutical composition which may comprise one or more antibodies or antigen-binding portions thereof, the immunoconjugates, bispecifics, CAR-expressing immune cells, nucleic acid molecules, expression vectors, or host cells of the present disclosure formulated together with a pharmaceutically acceptable carrier. The composition may optionally contain one or more additional pharmaceutically active ingredients, such as an anti-tumor agent, such as IMM01, a SIRPalphaD1-Fc fusion protein.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof.

The pharmaceutical composition may be suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody or antigen binding portion thereof, the dosage may range from about 0.0001 to 100 mg/kg.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies or antigen binding portions thereof of the disclosure can be formulated to ensure proper distribution in vivo. For example, to ensure that the therapeutic antibody or antigen binding portion thereof of the disclosure cross the blood-brain barrier, they can be formulated in liposomes, which may additionally comprise targeting moieties to enhance selective transport to specific cells or organs.

The pharmaceutical composition of the disclosure may have multiple in vitro and in vivo uses. For example, the pharmaceutical composition can be used to treat tumors, or more generally speaking, to enhance immune responses in tumor patients. The pharmaceutical composition may be administered to human subjects, to e.g., inhibit tumor growth.

Given the ability of the pharmaceutical composition to inhibit tumor cell proliferation and survival, the present application provides a method of inhibiting growth of tumor cells in a subject in need thereof, comprising administering to the subject the pharmaceutical composition of the disclosure, such that the tumor growth is inhibited in the subject. The tumor that may be treated by the pharmaceutical composition of the disclosure may be a solid tumor or a blood tumor, including, but not limited to, ovarian cancer, breast cancer, cervical cancer, endometrial cancer, acute lymphoblastic leukemia (ALL), pancreatic adenocarcinoma, cholangiocarcinoma, bladder cancer, pancreatic cancer, gastric adenocarcinoma, glioblastoma, and colon cancer, original or metastatic. The pharmaceutical composition of the disclosure may be administered with an additional anti-tumor agent, such as IMM01, a SIRPalpha-Fc fusion protein that binds CD47 and FcR and shows good anti-tumor efficacy.

Further, given the correlation between CD24 and inflammatory diseases, the present application provides a method for treating or ameliorating an inflammatory disease in a subject in need thereof, comprising administering to the subject the pharmaceutical composition of the disclosure. The inflammatory disease may be acute graft versus host disease, rheumatoid arthritis, or systemic lupus erythematosus.

The CD24 associated disease that can be treated by the pharmaceutical composition of the disclosure further includes, but not limited to, metabolic associated fatty liver disease, diabetes mellitus, multiple sclerosis, and sepsis.

The pharmaceutical composition of the disclosure may be administered with one or more additional agents that may effectively inhibit tumor growth or reduce/eliminate inflammation in a subject. In certain embodiments, the present application provides a method for inhibiting tumor growth in a subject in need thereof, comprising administering to the subject the pharmaceutical composition of the disclosure and IMM01, a SIRPalphaD1-Fc fusion protein.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present application is now further described with the non-limiting examples below.

EXAMPLES

The structures of the exemplary anti-CD24 antibodies of the disclosure, IMM47C, IMM47 and IMM47M, are shown in FIG. 1 and described below in further details.

IMM47C is an IgG antibody, comprising a mouse heavy chain variable region, a human IgG1 constant region, a mouse light chain variable region, and a human kappa constant region, respectively having the amino acid sequences of SEQ ID NOs: 7, 12, 8 and 13.

IMM47 is an IgG antibody, comprising a mouse heavy chain variable region, a human IgG1 constant region, a humanized light chain variable region, and a human kappa constant region, respectively having the amino acid sequences of SEQ ID NOs: 7, 12, 9 and 13.

IMM47H is an IgG antibody, comprising a humanized heavy chain variable region, a human IgG1 constant region, a humanized light chain variable region, and a human kappa constant region, respectively having the amino acid sequences of SEQ ID NOs: 10, 12, 11 and 13.

IMM01 is a SIRPαD1-Fc fusion protein that binds CD47, as disclosed in US2021/0024598A1, comprising two SIRPαD1 mutants linked to two Fc fragments, wherein each monomer of the formed dimer has the amino acid sequence of SEQ ID NO: 19. The SIRPαD1 mutant in IMM01 contains a N80A mutation in SEQ ID NO: 19 which removes a glycosylation site.

Example 1. Generation and Humanization of Anti-CD24 Antibodies, and Vector Construction for Antibody Expression Mice were immunized with human CD24 proteins, and those with good titers were selected for antibody preparation. Briefly, spleen cells from the selected mice were fused with myeloma cells, and hybridoma colonies that secreted anti-CD24 antibodies having high CD24 binding capabilities were picked out and subcloned by limited dilution. Monoclonal antibodies were generated and sequenced. One antibody, as referred to as IMM47C, had a heavy chain variable region and a light chain variable region with amino acid sequences set forth in SEQ ID NOs: 7 and 8, respectively.

IMM47C was later humanized using the well-established CDR-grafting method. An exemplary partially humanized antibody IMM47 and an exemplary humanized antibody IMM47H were obtained. IMM47 comprised a mouse heavy chain variable region and a humanized light chain variable region respectively having the amino acid sequences set forth in SEQ ID NOs: 7 and 9, while IMM47H comprised a humanized heavy chain variable region and a humanized light chain variable region respectively having the amino acid sequences set forth in SEQ ID NOs: 10 and 11.

The full length coding sequences of the exemplary antibodies were designed artificially.

Specifically, for IMM47C's heavy chain, 57 nucleotides encoding the signal peptide of mouse IgG1 heavy chain (SEQ ID NO: 21) were added to the 5' end of the coding sequence of IMM47C's heavy chain variable region plus constant region (SEQ ID NO: 14), and a Kozak sequence (SEQ ID NO: 22) was added to the 5' end of the signal peptide sequence. Lastly, HindIII and NheI restriction sites were added to the 5' and 3' ends of the resulting sequence, respectively. For IMM47C's light chain, the same signal sequence as well as the Kozak sequence was added to the 5' end of the coding sequence for IMM47C's light chain variable region plus constant region (SEQ ID NO: 15), and HindIII and XbaI restriction sites were added to the 5' and 3' ends of the resulting sequence, respectively. The sequences were synthesized by GenScript and cloned into pMac-H and pMac-L vectors, respectively.

For IMM47's heavy chain, 57 nucleotides encoding the signal peptide of mouse IgG1 heavy chain (SEQ ID NO: 21) were added to the 5' end of the coding sequence of IMM47's heavy chain variable region plus constant region (SEQ ID NO: 14), and a Kozak sequence (SEQ ID NO: 22) was added to the 5' end of the signal peptide sequence. Lastly, HindIII and NheI restriction sites were added to the 5' and 3' ends of the resulting sequence, respectively. For IMM47's light chain, the same signal sequence as well as the Kozak sequence was added to the 5' end of the coding sequence for IMM47's light chain variable region plus constant region (SEQ ID NO: 16), and HindIII and XbaI restriction sites were added to the 5' and 3' ends of the resulting sequence, respectively. The sequences were synthesized by GenScript and cloned into pMac-H and pMac-L vectors, respectively.

For IMM47H's heavy chain, 57 nucleotides encoding the signal peptide of mouse IgG1 heavy chain (SEQ ID NO: 21) were added to the 5' end of the coding sequence of IMM47H's heavy chain variable region plus constant region (SEQ ID NO: 17), and a Kozak sequence (SEQ ID NO: 22) was added to the 5' end of the signal peptide sequence. Lastly, HindIII and NheI restriction sites were added to the 5' and 3' ends of the resulting sequence, respectively. For IMM47H's light chain, the same signal sequence as well as the Kozak sequence was added to the 5' end of the coding sequence for IMM47H's light chain variable region plus constant region (SEQ ID NO: 18), and HindIII and XbaI restriction sites were added to the 5' and 3' ends of the resulting sequence, respectively. The sequences were synthesized by GenScript and cloned into pMac-H and pMac-L vectors, respectively.

These antibodies of the disclosure were expressed using CHO—S cells with the vectors constructed above. Briefly, CHO—S cells were seeded at a density of $1 \times 10^6$ cells/ml in TransFx-CTMCHO Transient transfection Medium (Hyclone) containing 6 mM glutamine one day before transient transfection. The heavy chain and light chain expression vectors, at a mass ratio of 1:1 with a total DNA amount of 1 μg/ml, were added to OPTI-MEM medium (Gibco) whose volume was 1/20 of that of the TransFx-CTMCHO Transient transfection Medium as used. PEI (polyethylenimine, MW 47,000, Cat #24765-1, polysciences) at 1 mg/ml was added to OPTI-MEM medium (Gibco) whose volume was 1/20 of that of the TransFx-CTMCHO Transient transfection Medium as used. The PEI dilution was slowly added to, mixed and incubated at room temperature for 20 min with the diluted DNAs, at a PEI: DNA mass ratio of 4:1. Then, the DNA/PEI mixture was added to the cell cultures, and the cells were incubated in a 37° C. and 5% $CO_2$ cell culture incubator with shaking at 110 rpm. Transfection enhancer (1 mM sodium butyrate, 0.25% V/V DMSO) was added two days later, and the temperature was decreased to 33° C. When the cell viability dropped to ~50%, the cell culture supernatant was harvested by centrifugation at 3000 rpm for 5 min, and subjected to protein purification using Protein A chromatography.

Example 2. Exemplary Antibody Bound to CD24$^+$ MCF-7 Cells

CD24$^+$ MCF-7 cells in 100 µl culture medium at a cell density of 1×10$^6$/ml were incubated with 100 µl serially diluted IMM47H and hIgG-Fc (3-fold dilution, starting at 30 µg/ml), respectively, at 4° C. for 1 h. Cells were washed with cold PBS twice, and then incubated with 100 µl FITC-conjugated secondary antibody against human IgG-Fc (Cat #F9512, Sigma) for 45 min. Cells were washed twice and re-suspended in 200 µl PBS. Then, the cells were subject to FACS analysis using a flow cytometer (Merck Millipore, Guava® easyCyte 5HT).

Figure 2:
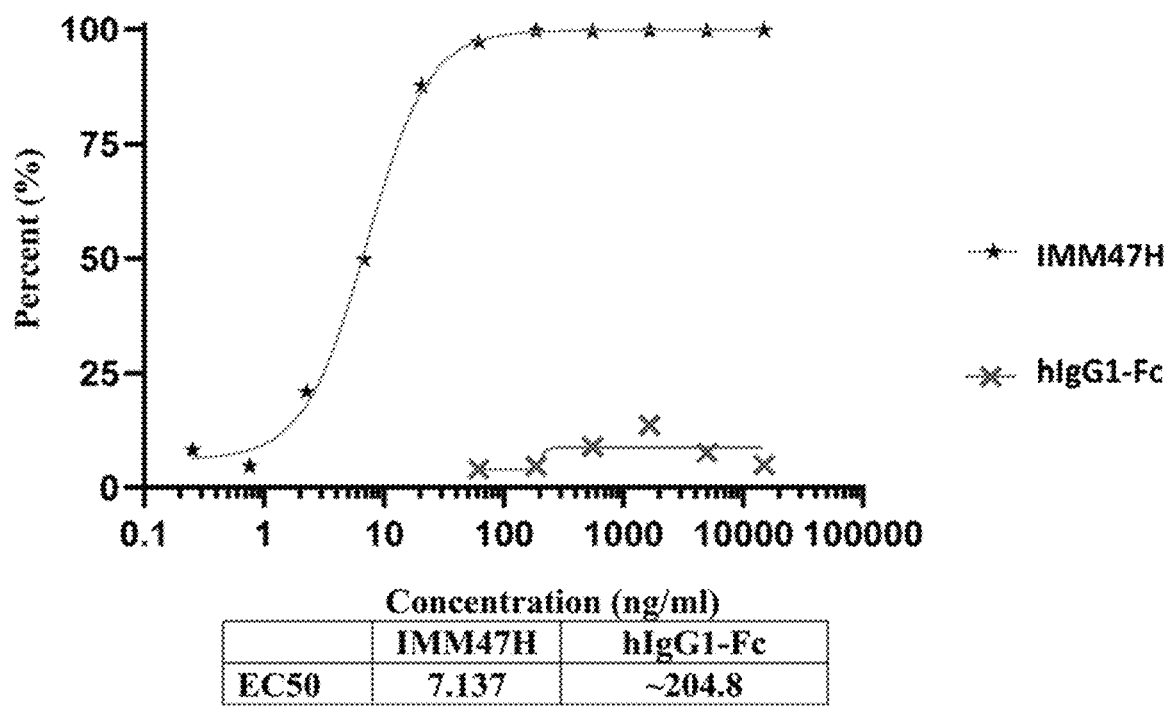
FIG. 2 shows the binding activity of IMM47H to $CD24^+$ MCF-7 cells, with hIgG-Fc used as the negative control.

As shown in FIG. 2, the anti-CD24 antibodies, including IMM47H, specifically bound to CD24$^+$ MCF-7 cells.

Example 3. Exemplary Antibody Bound to CD24$^+$ REH Cells

CD24$^+$ CD47$^+$ REH cells in 100 µl culture medium at a cell density of 1×10$^6$/ml were incubated with 100 µl serially diluted IMM47H, IMM01 and hIgG-Fc (3-fold dilution, starting at 30 µg/ml), respectively, at 4° C. for 1 h. Cells were washed with cold PBS twice, and then incubated with 100 µl FITC-conjugated secondary antibody against human IgG-Fc (Cat #F9512, Sigma) for 45 min. Cells were washed twice and re-suspended in 200 µl PBS. Then, the cells were subject to FACS analysis using a flow cytometer (Merck Millipore, Guava® easyCyte 5HT).

Figure 3:
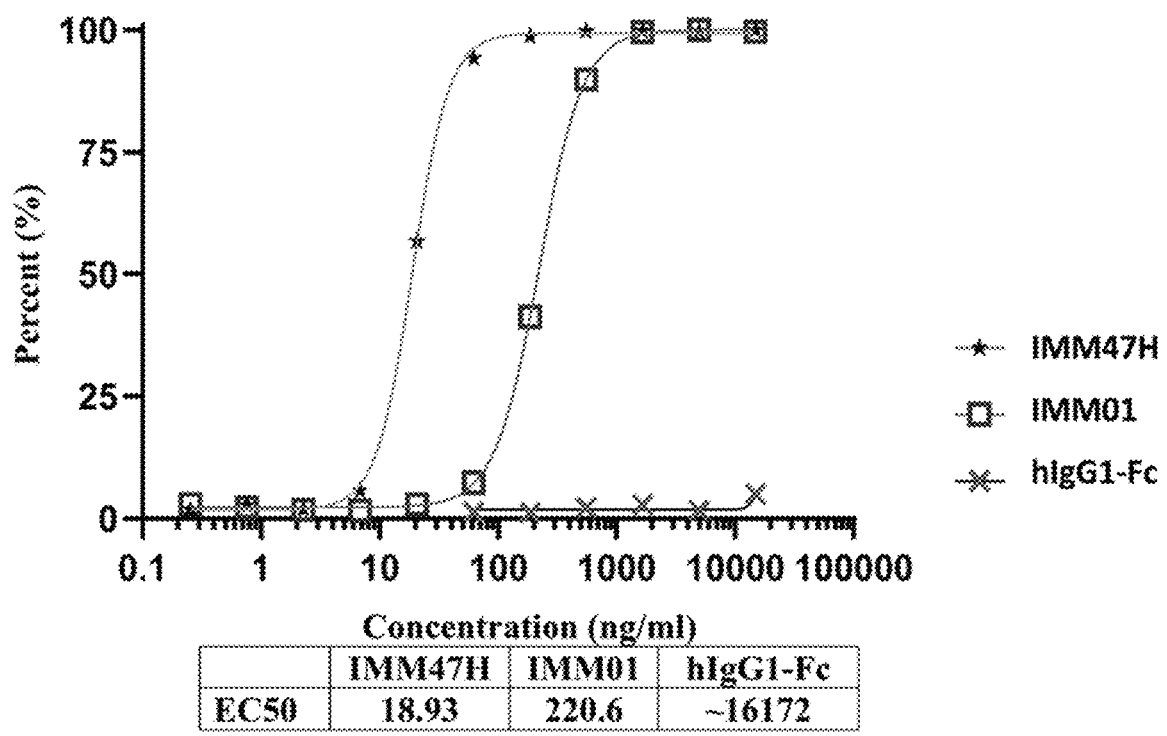
FIG. 3 shows the binding activity of IMM47H to $CD47^+$ $CD24^+$ REH cells, with IMM01 (SIRPalphaD1-F1, SEQ ID NO: 19) and hIgG-Fc used as the controls.

As shown in FIG. 3, the binding capability of IMM47H was a bit higher than that of IMM01, a CD47 binding protein.

Example 4. Exemplary Antibody Induced High Antibody-Dependent Cell-Mediated Cytotoxicity (ADCC) Against CD24+ MCF-7 Cells CFSE (Cat #21888-25 mg, Sigma) at 1 mM was 1:500 diluted and used to label MCF-7 cells.

Fifty µl of the CFSE-labeled MCF-7 cells, as the target cells, at 6×10$^5$/ml, were mixed at a 2:1 effector: target ratio with 100 µl 6×10$^5$/ml NK92MI cells stably expressing FcγRIIIa (158V), as the effector cells. The mixed cells were cultured for 4 hours at 37° C. under 5% $CO_2$ with 50 µl serially diluted IMM47C and hIgG-Fc (3-fold dilution, starting at 1000 ng/ml), respectively. Then cell cultures were added with propidium iodide (PI) (Cat #P4170, Sigma) at a concentration of 5 µg/ml, and then subjected to FACS analysis for PI signals. Percent cell lysis caused by ADCC was calculated based on the following formula:

% Lysis=(% PI Positive Target Cells treated with IMM47C−PI Positive Target Cells treated with negative control)/(100−PI Positive Target Cells treated with negative control)*100

Figure 4:
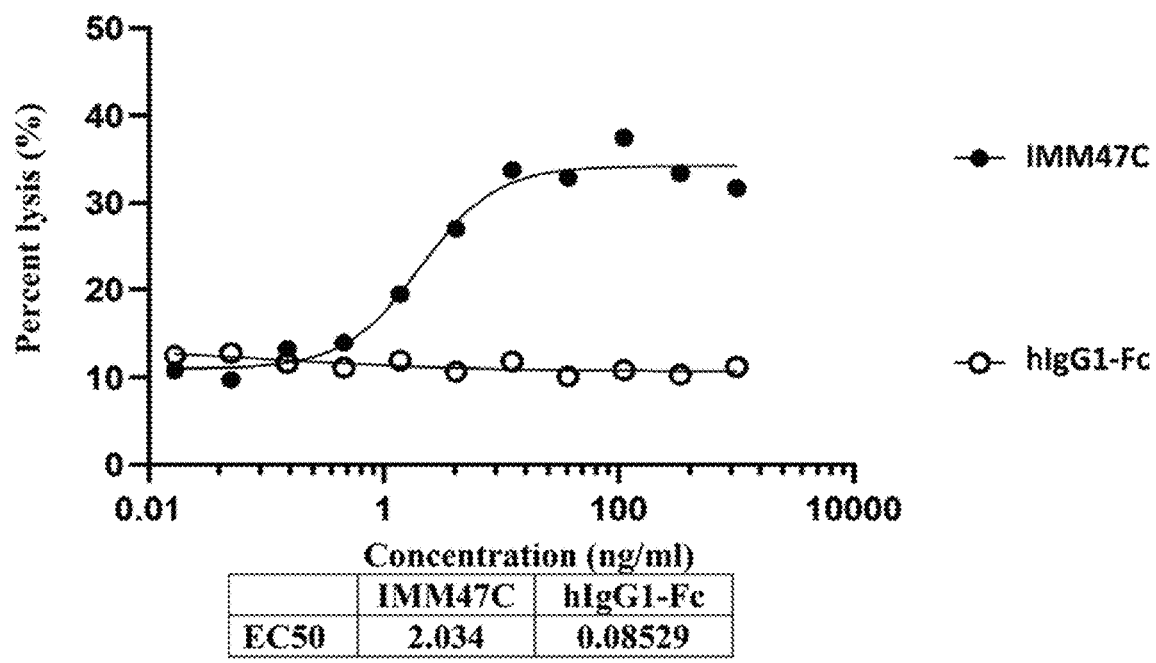
FIG. 4 shows the capability of IMM47C to induce antibody-dependent cellular cytotoxicity (ADCC) against $CD24^+$ MCF-7 cells, with hIgG1-Fc used as the negative control.

According to FIG. 4, IMM47C induced high ADCC against CD24+ MCF-7 cells.

Example 5. Exemplary Antibody Induced High Antibody-Dependent Cell-Mediated Cytotoxicity (ADCC) Against CD24$^+$ REH Cells CFSE (Cat #21888-25 mg, Sigma) at 1 mM was 1:500 diluted and used to label CD24$^+$CD47$^+$ REH cells.

Fifty µl of the CFSE-labeled REH cells, as the target cells, at 6×10$^5$/ml, were mixed at a 2:1 effector: target ratio with 100 µl 6×10$^5$/ml NK92MI cells stably expressing FcγRIIIa (158V), as the effector cells. The mixed cells were cultured for 4 hours at 37° C. under 5% $CO_2$ with 50 µl serially diluted IMM47C, IMM01 and hIgG-Fc (3-fold dilution, starting at 1000 ng/ml), respectively. Then cell cultures were added with propidium iodide (PI) (Cat #P4170, Sigma) at a concentration of 5 µg/ml, and then subjected to FACS analysis for PI signals.

Figure 5:
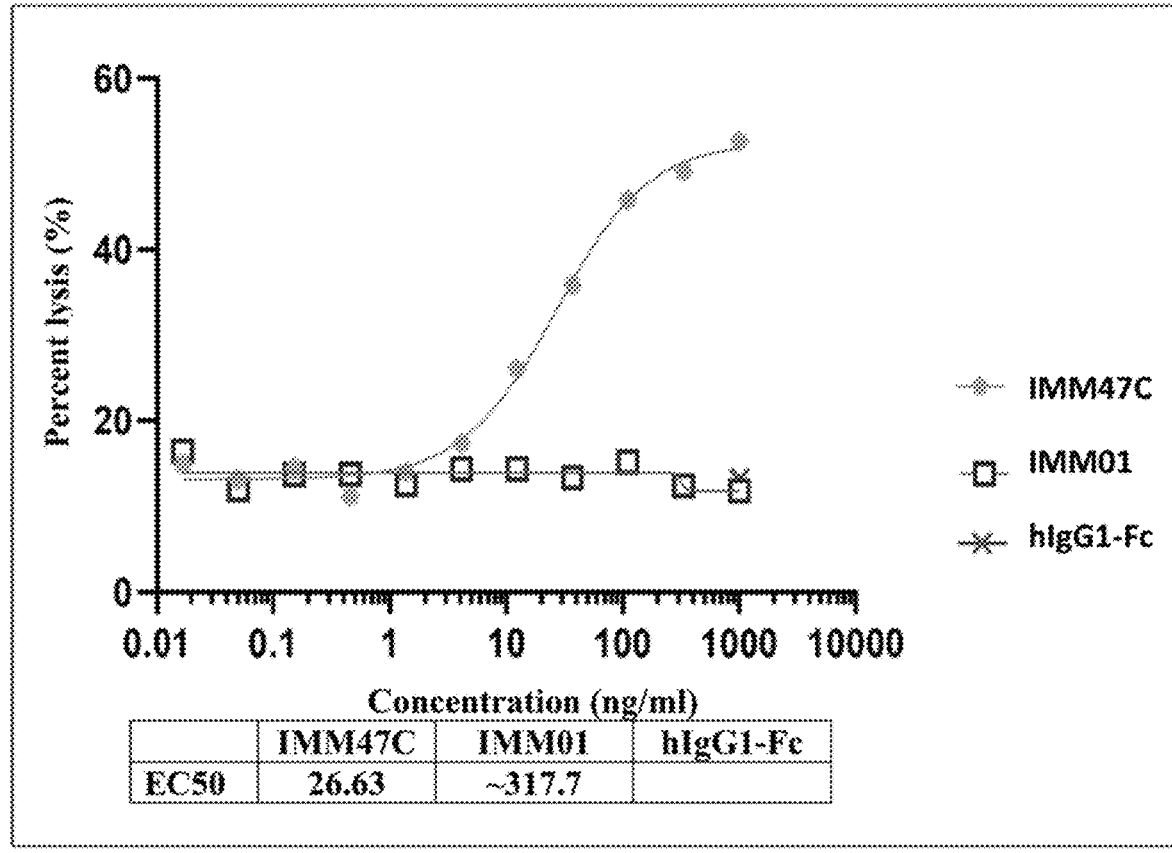
FIG. 5 shows the capability of IMM47C to induce antibody-dependent cellular cytotoxicity (ADCC) against $CD47^+CD24^+$ REH cells, with hIgG1-Fc and IMM01 used as the controls.

According to FIG. 5, IMM47C induced high ADCC against CD24$^+$ REH cells.

Example 6. Exemplary Antibody Induced High Antibody-Dependent Cell-Mediated Cytotoxicity (ADCC) Against CD24$^+$ MC38-hCD24 Cells CFSE (Cat #21888-25 mg, Sigma) at 1 mM was 1:500 diluted and used to label MC38 cells expressing human CD24 proteins.

Fifty µl of the CFSE-labeled MC38-hCD24 cells, as the target cells, at 6×10$^5$/ml, were mixed at a 2:1 effector: target ratio with 100 µl 6×10$^5$/ml NK92MI cells stably expressing FcγRIIIa (158V), as the effector cells. The mixed cells were cultured for 4 hours at 37° C. under 5% $CO_2$ with 50 µl serially diluted IMM47 and hIgG-Fc (3-fold dilution, starting at 1000 ng/ml), respectively. Then cell cultures were added with propidium iodide (PI) (Cat #P4170, Sigma) at a concentration of 5 µg/ml, and then subjected to FACS analysis for PI signals.

Figure 6:
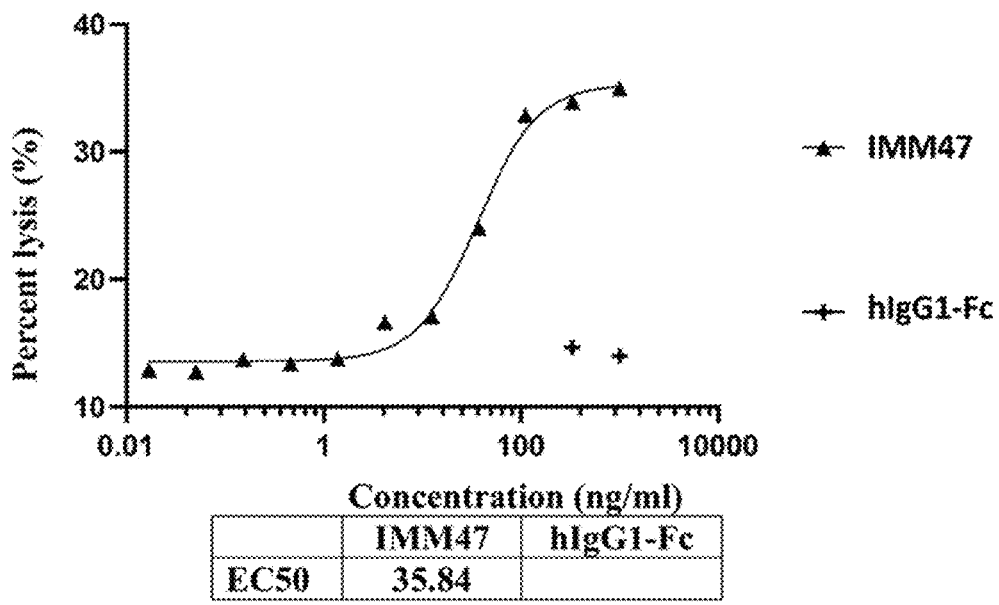
FIG. 6 shows the capability of IMM47 to induce antibody-dependent cellular cytotoxicity (ADCC) against MC38 cells engineered to express human CD24s, with hIgG1-Fc used as the negative control.

According to FIG. 6, IMM47 induced high ADCC against MC38-hCD24 cells.

Example 7. Exemplary Antibody Showed Potent Anti-Tumor Activity in Breast Cancer Model Thirty-two 6-8-week-old SCID mice each had a 0.36 mg beta-estradiol delayed-release tablet embedded at the left back, 3 days before subcutaneous injection of MCF-7 cells, 1×10$^7$ cells per mouse, at the right axilla. When tumor sizes reached 100-150 mm$^3$, mice were randomly allocated into 4 groups with 8 mice per group, and this day was designated as Day 0. From that day on, mice were respectively given intraperitoneal injection of PBS, IMM47C (2.5 mg/kg), IMM01 (2.5 mg/kg), and IMM01+IMM47C (2.5 mg/kg+2.5 mg/kg), for 4 weeks, twice per week. Administration was stopped at the end of week 4 and mice were observed till termination of experiment when the average tumor volume in the PBS group reached 3000 mm$^3$. Tumor sizes and body weights were measured every 3-4 days.

The tumor volume (V) was calculated as (length×width$^2$)/2. Tumor growth inhibition rate (TGI) was calculated by the formula: TGI (%)=(1−tumor volume change in administration group/tumor volume change in vehicle control group)×100%.

The test regime and results were summarized in Table 1.

TABLE 1

Anti-tumor effects of IMM47C and other agents

| Group | Drug | Animal# | Dose (mg/kg) | Treatment | TGI | P value |
|---|---|---|---|---|---|---|
| 1 | PBS | 8 | n/a | i.p.b.w. × 4 | | |
| 2 | IMM01 | 8 | 2.5 | i.p.b.w. × 4 | 17.19% | 0.375 |
| 3 | IMM47C | 8 | 2.5 | i.p.b.w. × 4 | 37.30% | 0.009 |
| 4 | IMM01 + IMM47C | 8 | 2.5 + 2.5 | i.p.b.w. × 4 | 92.22% | 0.001 |

On Day 28, the average tumor size of mice in Group 1 (PBS) was 646.87 mm$^3$. Compared to the vehicle control group, both IMM47C and IMM01 treatments slowed tumor growth rate. These two groups had average tumor sizes at 463.26 mm$^3$ (T/C=71.60%, TGI=37.30%, p=0.009) and 562.24 mm$^3$ (T/C=86.92%, TGI=17.19%, p=0.375), respectively, on Day 28. IMM47C+IMM01 administration showed the best tumor suppression effects, the mice in this group had the average tumor size at 192.63 mm$^3$ (T/C=29.81%, TGI=92.22%, p=0.001), on Day 28.

Figure 7:
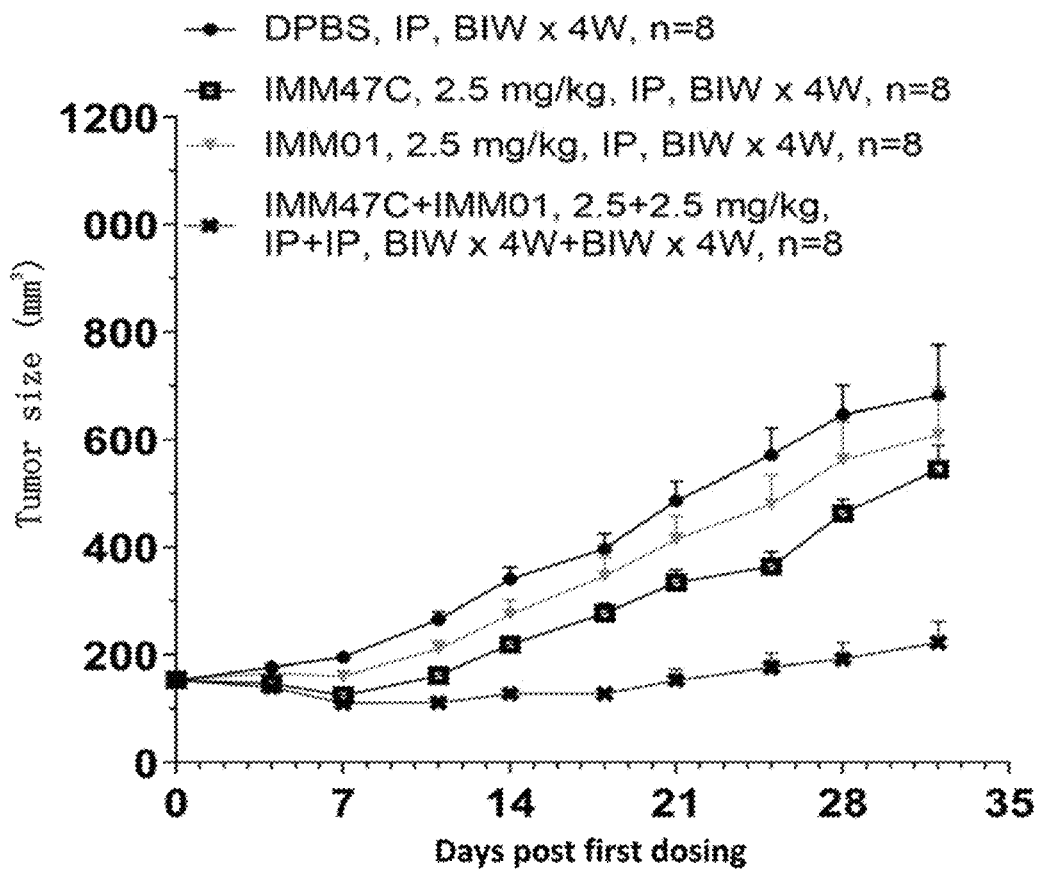
FIG. 7 shows the in vivo anti-tumor efficacy of IMM47C and the IMM47C+IMM01 combination in CB17-SCID mice engrafted with $CD24^+CD47^+$ MCF-7 cells.

It can be seen from Table 1 and FIG. 7 that IMM47 had potent anti-tumor effect, and synergized with IMM01 to provide an anti-tumor effect that was much better than IMM47 alone and IMM01 alone.

Example 8. Exemplary Antibody Showed Potent Anti-Tumor Activity in Colon Cancer Model B6 male transgenic mice (engineered to express human Siglec10) were each injected with 100 μl 1.0×10$^7$/ml MC38-hCD24 cells at the right axilla. When tumor sizes reached about 100 mm$^3$, the mice were randomly allocated into 3 groups with 10 mice per group, and this day was designated as Day 0. From that day on, mice were respectively given intraperitoneal injection of PBS, IMM47H (10 mg/kg), and IMM47C (10 mg/kg), twice per week. After 4 doses, 7 mice were randomly picked from each group and injected with 1.0×10$^6$ MC38-hCD24 cells again at the left axilla, and were no longer given antibody treatment. The mice were observed twice a week for their physical conditions and tumor growth. Any mouse bearing a tumor having a size over 3000 mm$^3$ would be removed from the test and subject to euthanasia.

Figure 8A:
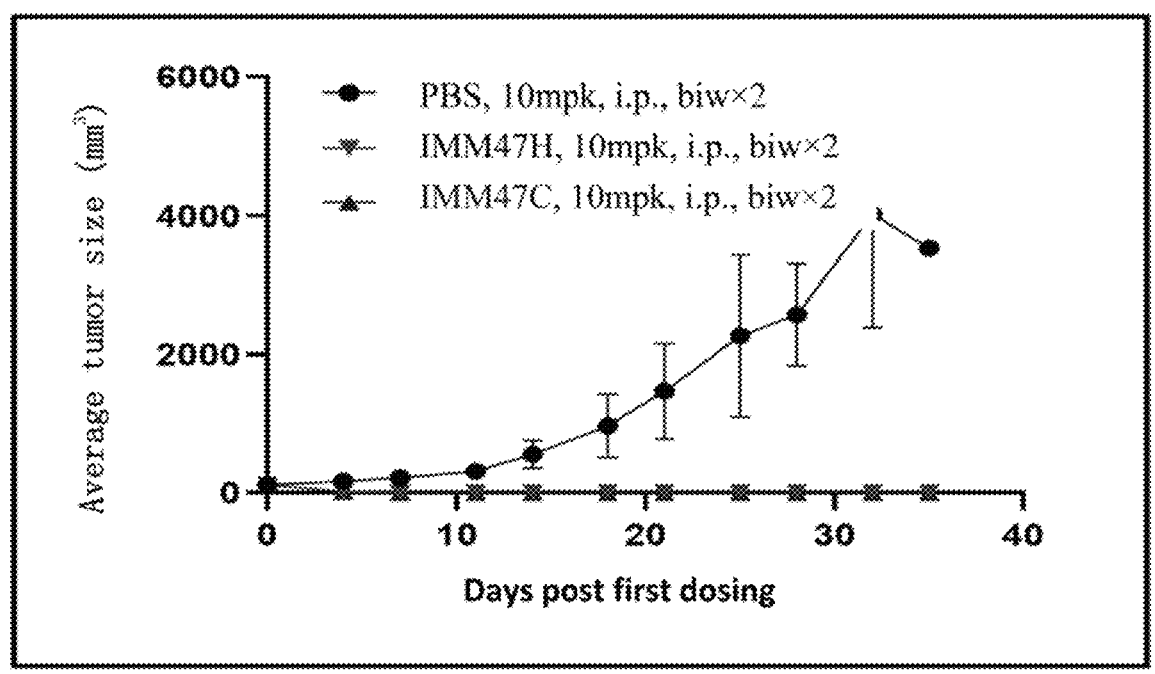
FIGS. 8A and 8B show the anti-tumor efficacy of IMM47H and IMM47C in B6 transgenic mice (engineered to express human Siglec10) engrafted with MC38-hCD24 cells, as revealed by the average tumor size (A) and individual tumor sizes (B) in each group.
Figure 8B:
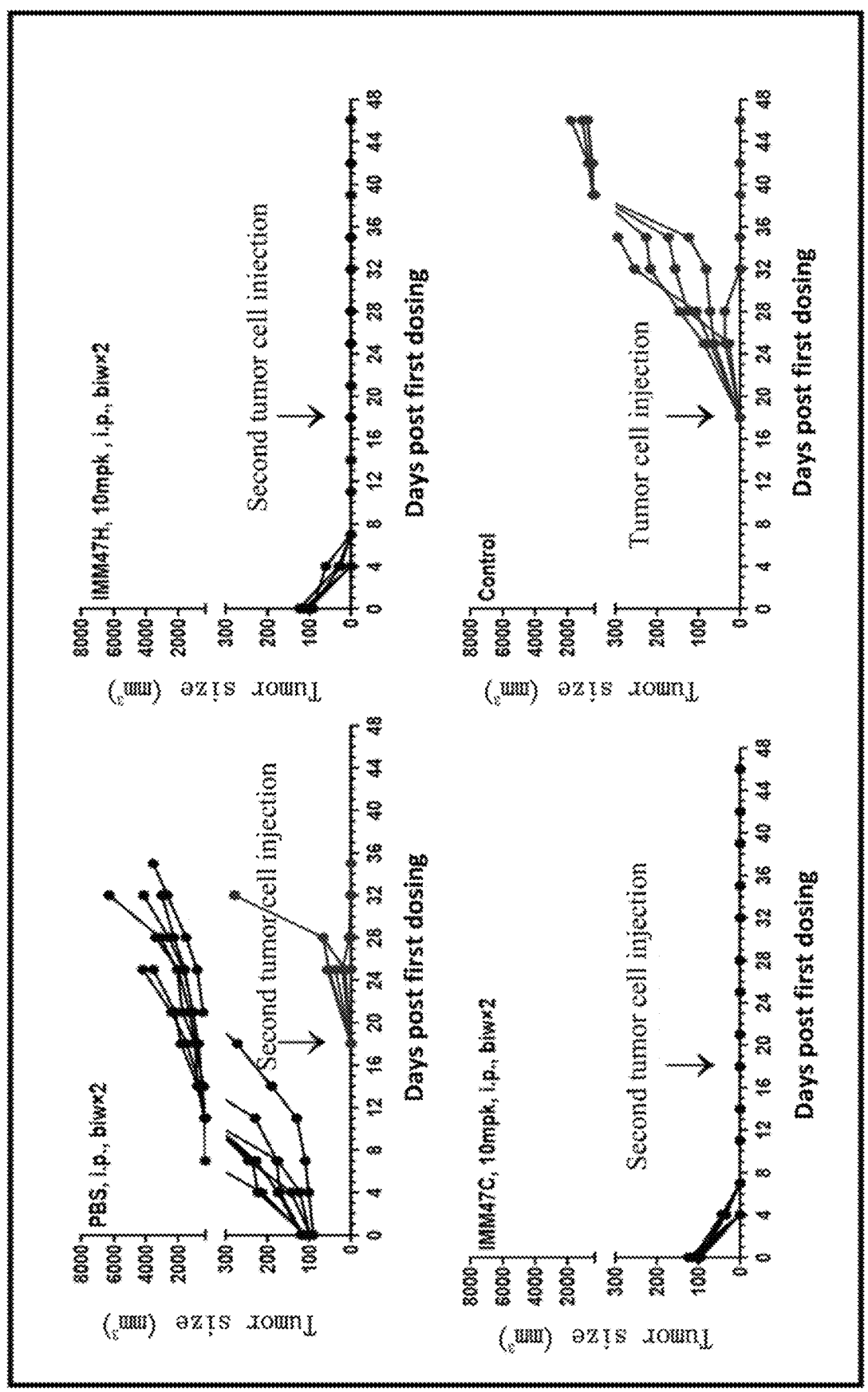

The test regime was summarized in Table 2 and FIG. 8B.

TABLE 2

Anti-tumor effects of IMM47H, IMM47C and other agents

| Group | Drug | Dose (mg/kg) | Treatment | Tumor size (D 18) | TGI | P value |
|---|---|---|---|---|---|---|
| 1 | PBS | n/a | i.p., biw. × 2 | 969.92 ± 143.93 | — | — |
| 2 | IMM47H | 10 mg/kg | i.p., biw. × 2 | 0.00 ± 0.00 | 113.22% | <0.01 |
| 3 | IMM47C | 10 mg/kg | i.p., biw. × 2 | 0.00 ± 0.00 | 113.25% | <0.01 |

As shown in Table 2 and FIGS. 8A-8B, the tumors in the mice were completely eliminated after 4 doses of IMM47H or IMM47C, while the vehicle control group had an average tumor size of 969.92±143.93 mm$^3$ New tumors formed in 5 out of 7 mice from the PBS group after the second injection of MC38-hCD24 cells on Day 18, while no tumor was formed in mice from the IMM47H or IMM47C group.

The data suggested that IMM47C and IMM47H can significantly suppress tumor growth in B6-Siglec10 transgenic mice engrafted with MC38-hCD24 cells, and adaptive immune responses may be triggered in mice from the IMM47H and IMM47C treatment groups when they were given the second injection of tumor cells.

Example 9. Exemplary Antibody Showed Potent Anti-Tumor Activity in Colon Cancer Model Twenty-four B6 male transgenic mice (engineered to express human Siglec10) were each injected with 100 μl 1.0×10$^7$ ml MC38-hCD24 cells at the right axilla. When tumor sizes reached about 100 mm$^3$, the mice were randomly allocated into 4 groups with 6 mice per group, and this day was designated as Day 0. From that day on, mice were respectively given intraperitoneal injection of PBS, IMM47 (3 mg/kg), IMM47H (3 mg/kg), and IMM47C (3 mg/kg), for 4 weeks, twice per week.

As some mice's tumor sizes exceeded the preset threshold at Day 21, the data from Day 0 to Day 21 were used for analysis.

Figure 9:
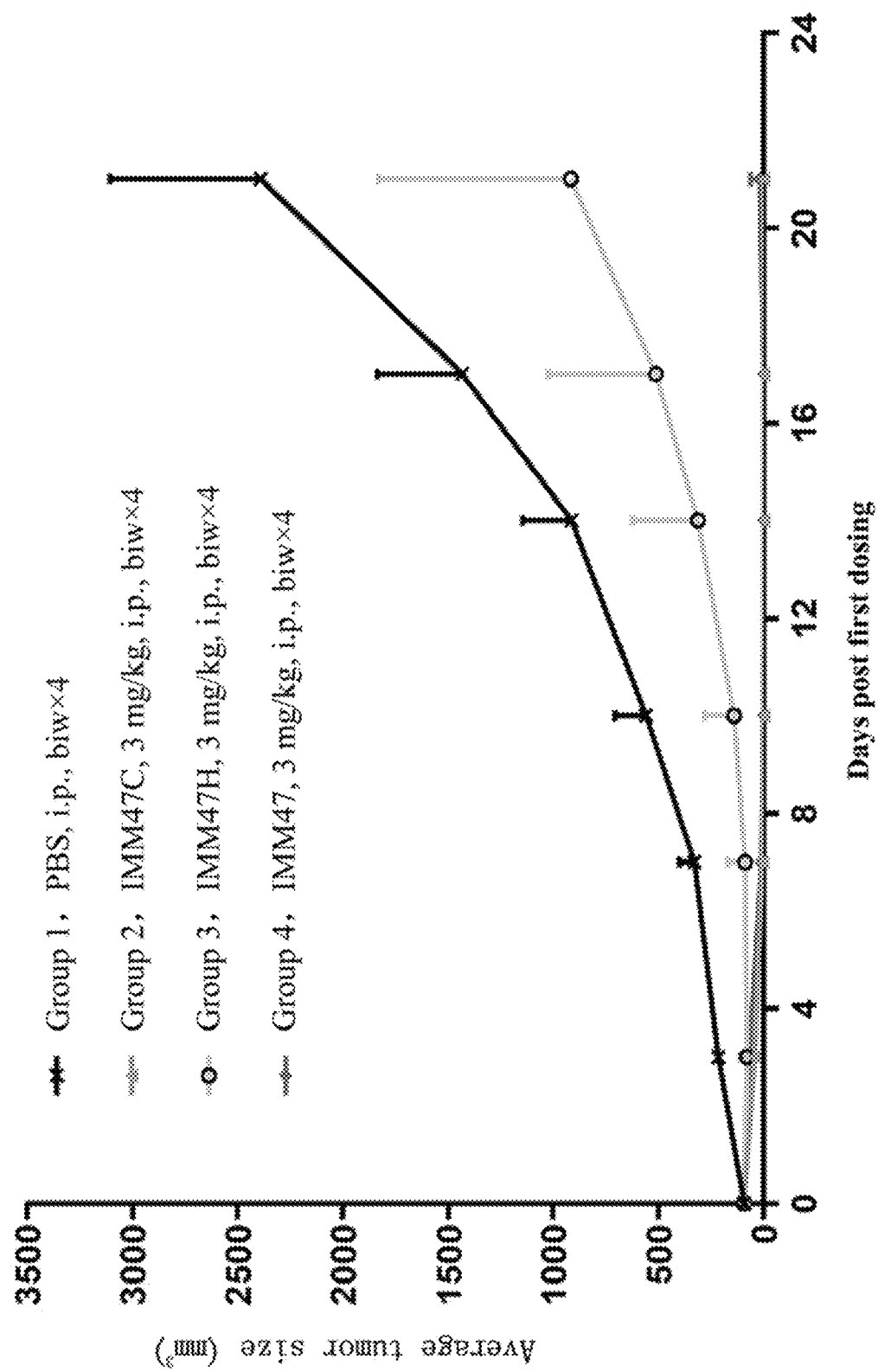
FIG. 9 shows the anti-tumor effects of IMM47C, IMM47 and IMM47H in B6-Siglec10 transgenic mice engrafted with MC38-hCD24 cells.

The test regime and results were summarized in Table 3 and FIG. 9.

TABLE 3

Anti-tumor effects of IMM47, IMM47H, IMM47C and other agents

| Group | Drug | Dose (mg/kg) | Treatment | Tumor size (D 21) | TGI | P value |
|---|---|---|---|---|---|---|
| 1 | PBS | n/a | i.p., biw. × 4 | 2392.33 ± 714.66 | — | — |
| 2 | IMM47C | 3 mg/kg | i.p., biw. × 4 | 0.00 ± 0.00 | 104.06% | <0.01 |
| 3 | IMM47H | 3 mg/kg | i.p., biw. × 4 | 915.04 ± 915.04 | 64.26% | =0.232 |
| 4 | IMM47 | 3 mg/kg | i.p., biw. × 4 | 20.58 ± 16.93 | 103.16% | <0.01 |

As shown in Table 3 and FIG. 9, IMM47, IMM47C and IMM47H can significantly suppress tumor growth in B6-Siglec10 transgenic mice engrafted with MC38-hCD24 cells. Specifically, at the dose of 3 mg/kg, the tumors were completely removed in all 6 mice from the IMM47C group, 4 from the IMM47 group and 5 from the IMM47H group, and the tumors in 2 mice from the IMM47 group grew slowly.

The sequences of the application were set forth below.

```
Description/Sequence/SEQ ID NO.

HV-CDR-1 of IMM47C, IMM47 and IMM47H
GYSITSGYS (SEQ ID NO: 1)

HV-CDR-2 of IMM47C, IMM47 and IMM47H
IHYSGST (SEQ ID NO: 2)

HV-CDR-3 of IMM47C, IMM47 and IMM47H
ARGADYALDY (SEQ ID NO: 3)

LV-CDR-1 of IMM47C, IMM47 and IMM47H
QSLLYSSNQKNY (SEQ ID NO: 4)

LV-CDR-2 of IMM47C, IMM47 and IMM47H
WAS (SEQ ID NO: 5)

LV-CDR-3 of IMM47C, IMM47 and IMM47H
QQNFIYPLT (SEQ ID NO: 6)

IMM47C/IMM47's heavy chain variable region
DVQLQESGPDLVKPSQSLSLTCTVTGYSITSGYSWHWIRQFPGNKLEWMGYIHYSGSTKYNPSLKSRISITRD
TSKNQFFLQLNSVTTEDTATYFCARGADYALDYWGQRTSVTVSS (SEQ ID NO: 7)

IMM47C's light chain variable region
DIVMSQSPSSLAVSVGEKVTMSCKSSQSLLYSSNQKNYLAWYQQKPGHSPKLLIYWASTRESGVPDRFTGSGS
GTDFTLTISSVKAEDLAVYYCQQNFIYPLTFGAGTKLELK (SEQ ID NO: 8)

IMM47's light chain variable region
DIQMTQSPSSLSASVGDRVTITCKSSQSLLYSSNQKNYLAWYQQKPGKAPKLLIYWASTRESGVPSRFSGSGS
GTDFTLTISSLQPEDFATYYCQQNFIYPLTFGGGTKVELK (SEQ ID NO: 9)

IMM47H's heavy chain variable region
DVQLQESGPGLVKPSETLSLTCTVSGYSITSGYSWHWIRQPPGKGLEWIGYIHYSGSTKYNPSLKSRVTISVD
TSKNQFSLKLSSVTAADTAVYYCARGADYALDYWGQRTSVTVSS (SEQ ID NO: 10)

IMM47H's light chain variable region
DIVMTQSPDSLAVSLGERATINCKSSQSLLYSSNQKNYLAWYQQKPGQPPKLLIYWASTRESGVPDRFSGSGS
GTDFTLTISSLQAEDVAVYYCQQNFIYPLTFGGGTKVELK (SEQ ID NO: 11)

Heavy chain constant region
ASTKGPSVFPLAPSSKSTSGGTAALGCLVKDYFPEPVTVSWNSGALTSGVHTFPAVLQSSGLYSLSSVVTVPS
SSLGTQTYICNVNHKPSNTKVDKRVEPKSCDKTHTCPPCPAPELLGGPSVFLFPPKPKDTLMISRTPEVTCVV
VDVSHEDPEVKFNWYVDGVEVHNAKTKPREEQYNATYRVVSVLTVLHQDWLNGKEYKCKVSNKALPAPIAATI
SKAKGQPREPQVYTLPPSREEMTKNQVSLTCLVKGFYPSDIAVEWESNGQPENNYKTTPPVLDSDGSFFLYSK
LTVDKSRWQQGNVFSCSVMHEALHNHYTQKSLSLSPGK (SEQ ID NO: 12)

Light chain constant region
RTVAAPSVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQ ID NO: 13)

IMM47C/IMM47's heavy chain
ATGAGAGTGCTGATTCTTTTGTGCCTGTTCACAGCCTTTCCTGGTATCCTGTCTGATGTGCAGCTTCAGGAGT
CAGGACCTGACCTGGTGAAACCTTCTCAGTCACTTTCACTCACCTGCACTGTCACTGGCTACTCCATCACCAG
```

| Description/Sequence/SEQ ID NO. |
| --- |
| TGGTTATAGCTGGCACTGGATCCGGCAGTTTCCAGGAAACAAACTGGAATGGATGGGCTACATACACTATAGT<br>GGTAGCACTAAGTACAACCCATCTCTCAAAAGTCGAATCTCTATCACTCGAGACACATCCAAGAACCAGTTCT<br>TCCTGCAGTTGAATTCTGTGACTACTGAGGACACAGCCACATATTTCTGTGCAAGAGGCGCGGACTATGCTTT<br>GGACTACTGGGGTCAACGAACCTCAGTCACCGTCTCCTCAGCTAGCACCAAGGGCCCATCGGTCTTCCCCCTG<br>GCACCCTCCTCCAAGAGCACCTCTGGGGGCACAGCGGCCCTGGGCTGCCTGGTCAAGGACTACTTCCCCGAAC<br>CGGTGACGGTGTCGTGGAACTCAGGCGCCCTGACCAGCGGCGTGCACACCTTCCCGGCTGTCCTACAGTCCTC<br>AGGACTCTACTCCCTCAGCAGCGTGGTGACCGTGCCCTCCAGCAGCTTGGGCACCCAGACCTACATCTGCAAC<br>GTGAATCACAAGCCCAGCAACACCAAGGTGGACAAGAGAGTTGAGCCCAAATCTTGTGACAAAACTCACACAT<br>GCCCACCGTGCCCAGCACCTGAACTCCTGGGGGGACCGTCAGTCTTCCTCTTCCCCCCAAAACCCAAGGACAC<br>CCTCATGATCTCCCGGACCCCTGAGGTCACATGCGTGGTGGTGGACGTGAGCCACGAAGACCCTGAGGTCAAG<br>TTCAACTGGTATGTGGACGGCGTGGAGGTGCATAATGCCAAGACAAAGCCGCGGGAGGAGCAGTACAACGCCA<br>CGTACCGTGTGGTCAGCGTCCTCACCGTCCTGCACCAAGACTGGCTGAATGGCAAGGAGTACAAGTGCAAGGT<br>CTCCAACAAAGCCCTCCCAGCCCCCATCGCCGCAACCATCTCCAAAGCCAAAGGGCAGCCCCGAGAACCACAG<br>GTGTACACCCTGCCCCCATCCCGGGAGGAGATGACCAAGAACCAAGTCAGCCTGACCTGCCTGGTCAAAGGCT<br>TCTATCCCAGCGACATCGCCGTGGAGTGGGAGAGCAATGGGCAGCCGGAGAACAACTACAAGACCACGCCTCC<br>CGTGCTGGACTCCGACGGCTCCTTCTTCCTCTATTCCAAGCTCACCGTGGACAAGAGCAGGTGGCAGCAGGGG<br>AACGTCTTCTCATGCTCCGTGATGCATGAGGCTCTGCACAACCACTACACGCAGAAGAGCCTCTCCCTGTCTC<br>CGGGCAAATGA (SEQ ID NO: 14) |
| |
| IMM47C's light chain |
| ATGGATTCACAGGCCCAGGTTCTTATGTTACTGCTGCTATGGGTATCTGGTACCTGTGGGGACATTGTGATGT<br>CACAGTCTCCATCCTCCCTAGCTGTGTCAGTTGGAGAGAAGGTTACTATGAGCTGCAAGTCCAGTCAGAGCCT<br>TTTATATAGTAGCAATCAAAAGAACTACTTGGCCTGGTACCAGCAGAAACCAGGGCACTCTCCTAAACTGCTG<br>ATTTACTGGGCATCCACTAGGGAATCTGGGGTCCCTGATCGCTTCACAGGCAGTGGATCTGGGACAGATTTCA<br>CTCTCACCATCAGCAGTGTGAAGGCTGAAGACCTGGCAGTTTATTACTGTCAGCAAAATTTTATCTATCCGCT<br>CACGTTCGGTGCTGGGACCAAGCTGGAGCTGAAACGTGAGTTCTAGAGGATCCATCTGGGATAAGCATGCTGT<br>TTTCTGTCTGTCCCTAACATGCCCTGTGATTATCCGCAAACAACACACCCAAGGGCAGAACTTTGTTACTTAA<br>ACACCATCCTGTTTGCTTCTTTCCTCAGGAACTGTGGCTGCACCATCTGTCTTCATCTTCCCGCCATCTGATG<br>AGCAGTTGAAATCTGGAACTGCCTCTGTTGTGTGCCTGCTGAATAACTTCTATCCCAGAGAGGCCAAAGTACA<br>GTGGAAGGTGGATAACGCCCTCCAATCGGGTAACTCCCAGGAGAGTGTCACAGAGCAGGACAGCAAGGACAGC<br>ACCTACAGCCTCAGCAGCACCCTGACGCTGAGCAAAGCAGACTACGAGAAACACAAAGTCTACGCCTGCGAAG<br>TCACCCATCAGGGCCTGAGCTCGCCCGTCACAAAGAGCTTCAACAGGGGAGAGTGTTAG<br>(SEQ ID NO: 15) |
| |
| IMM47's light chain |
| ATGGGATGGTCATGTATCATCCTTTTTCTGGTAGCAACTGCAACTGGAGTACATTCAGACATTCAGATGACAC<br>AGAGCCCTAGCAGCCTGAGCGCCTCCGTGGGCGACAGAGTGACCATCACCTGCAAGAGCAGCCAAAGCCTGCT<br>GTACAGCAGCAATCAGAAGAACTACCTGGCCTGGTATCAGCAGAAGCCTGGCAAGGCCCCTAAGCTGCTGATC<br>TACTGGGCCTCCACAAGAGAGAGCGGCGTGCCTAGCAGATTCAGCGGCAGCGGCAGCGGCACCGACTTCACCC<br>TGACCATCAGCAGCCTGCAGCCTGAGGACTTCGCCACCTACTACTGTCAGCAGAACTTCATCTACCCTCTGAC<br>CTTCGGCGGAGGCACCAAGGTGGAGCTGAAGCGTGAGTTCTAGAGGATCCATCTGGGATAAGCATGCTGTTTT<br>CTGTCTGTCCCTAACATGCCCTGTGATTATCCGCAAACAACACACCCAAGGGCAGAACTTTGTTACTTAAACA<br>CCATCCTGTTTGCTTCTTTCCTCAGGAACTGTGGCTGCACCATCTGTCTTCATCTTCCCGCCATCTGATGAGC<br>AGTTGAAATCTGGAACTGCCTCTGTTGTGTGCCTGCTGAATAACTTCTATCCCAGAGAGGCCAAAGTACAGTG<br>GAAGGTGGATAACGCCCTCCAATCGGGTAACTCCCAGGAGAGTGTCACAGAGCAGGACAGCAAGGACAGCACC<br>TACAGCCTCAGCAGCACCCTGACGCTGAGCAAAGCAGACTACGAGAAACACAAAGTCTACGCCTGCGAAGTCA<br>CCCATCAGGGCCTGAGCTCGCCCGTCACAAAGAGCTTCAACAGGGGAGAGTGTTAG (SEQ ID NO: 16) |
| |
| IMM47H's heavy chain |
| ATGGGATGGTCATGTATCATCCTTTTTCTGGTAGCAACTGCAACTGGAGTACATTCAGACGTGCAGCTGCAAG<br>AGAGCGGCCCTGGCCTGGTGAAGCCTAGCGAGACCCTGAGCCTGACCTGCACCGTGTCCGGCTACAGCATCAC<br>AAGCGGCTACAGCTGGCACTGGATCAGACAGCCTCCTGGCAAGGGCCTGGAGTGGATCGGCTACATCCACTAC<br>AGCGGCAGCACCAAGTACAACCCTAGCCTGAAGAGCAGAGTGACCATCAGCGTGGACACAAGCAAGAATCAGT<br>TCAGCCTGAAGCTGAGCAGCGTGACCGCCGCCGACACCGCCGTGTACTACTGCGCTAGAGGCGCCGACTACGC<br>CCTGGACTACTGGGGACAGAGAACAAGCGTGACCGTGAGCAGCGCTAGCACCAAGGGCCCATCGGTCTTCCCC<br>CTGGCACCCTCCTCCAAGAGCACCTCTGGGGGCACAGCGGCCCTGGGCTGCCTGGTCAAGGACTACTTCCCCG<br>AACCGGTGACGGTGTCGTGGAACTCAGGCGCCCTGACCAGCGGCGTGCACACCTTCCCGGCTGTCCTACAGTC<br>CTCAGGACTCTACTCCCTCAGCAGCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCCCAAATCTTGTGACAAAACTCACA<br>CATGCCCACCGTGCCCAGCACCTGAACTCCTGGGGGGACCGTCAGTCTTCCTCTTCCCCCCAAAACCCAAGGA<br>CACCCTCATGATCTCCCGGACCCCTGAGGTCACATGCGTGGTGGTGGACGTGAGCCACGAAGACCCTGAGGTC<br>AAGTTCAACTGGTATGTGGACGGCGTGGAGGTGCATAATGCCAAGACAAAGCCGCGGGAGGAGCAGTACAACG<br>CCACGTACCGTGTGGTCAGCGTCCTCACCGTCCTGCACCAAGACTGGCTGAATGGCAAGGAGTACAAGTGCAA<br>GGTCTCCAACAAAGCCCTCCCAGCCCCCATCGCCGCAACCATCTCCAAAGCCAAAGGGCAGCCCCGAGAACCA<br>CAGGTGTACACCCTGCCCCCATCCCGGGAGGAGATGACCAAGAACCAAGTCAGCCTGACCTGCCTGGTCAAAG<br>GCTTCTATCCCAGCGACATCGCCGTGGAGTGGGAGAGCAATGGGCAGCCGGAGAACAACTACAAGACCACGCC<br>TCCCGTGCTGGACTCCGACGGCTCCTTCTTCCTCTATTCCAAGCTCACCGTGGACAAGAGCAGGTGGCAGCAG<br>GGGAACGTCTTCTCATGCTCCGTGATGCATGAGGCTCTGCACAACCACTACACGCAGAAGAGCCTCTCCCTGT<br>CTCCGGGCAAATGA (SEQ ID NO: 17) |
| |
| IMM47H's light chain |
| ATGGGATGGTCATGTATCATCCTTTTTCTGGTAGCAACTGCAACTGGAGTACATTCAGACATCGTGATGACAC<br>AGAGCCCTGACAGCCTGGCCGTGAGCCTGGGCGAGAGAGCCACCATCAACTGCAAGAGCTCTCAGAGCCTGCT<br>GTACAGCAGCAATCAGAAGAACTACCTGGCCTGGTATCAGCAGAAGCCTGGACAGCCTCCTAAGCTGCTGATC<br>TACTGGGCAAGCACAAGAGAGAGCGGCGTGCCTGACAGATTCAGCGGCAGCGGCAGCGGCACCGACTTCACCC<br>TGACCATCAGCAGCCTGCAAGCCGAGGACGTGGCCGTGTACTACTGTCAGCAGAACTTCATCTACCCTCTGAC<br>CTTCGGCGGCGGCACCAAGGTGGAGCTGAAGCGTGAGTTCTAGAGGATCCATCTGGGATAAGCATGCTGTTTT |

| Description/Sequence/SEQ ID NO. |
|---|
| CTGTCTGTCCCTAACATGCCCTGTGATTATCCGCAAACAACACACCCAAGGGCAGAACTTTGTTACTTAAACA<br>CCATCCTGTTTGCTTCTTTCCTCAGGAACTGTGGCTGCACCATCTGTCTTCATCTTCCCGCCATCTGATGAGC<br>AGTTGAAATCTGGAACTGCCTCTGTTGTGTGCCTGCTGAATAACTTCTATCCCAGAGAGGCCAAAGTACAGTG<br>GAAGGTGGATAACGCCCTCCAATCGGGTAACTCCCAGGAGAGTGTCACAGAGCAGGACAGCAAGGACAGCACC<br>TACAGCCTCAGCAGCACCCTGACGCTGAGCAAAGCAGACTACGAGAAACACAAAGTCTACGCCTGCGAAGTCA<br>CCCATCAGGGCCTGAGCTCGCCCGTCACAAAGAGCTTCAACAGGGGAGAGTGTTAG (SEQ ID NO: 18) |
| SIRPalphaD1 mutant-Fc (IMM01)<br>EEELQVIQPDKSVSVAAGESAILHCTVTSLIPVGPIQWFRGAGPARELIYNQKEGHFPRVTTVSESTKRENMD<br>FSISISAITPADAGTYYCVKFRKGSPDTEFKSGAGTELSVRAKPSAPVVSGPAARATPQHEPKSCDKTHTCPP<br>CPAPELLGGPSVFLFPPKPKDTLMISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLPPSRDELTKNQVSLTCLVKGFYP<br>SDIAVEWESNGQPENNYKTTPPVLDSDGSFFLYSKLTVDKSRWQQGNVFSCSVMHEALHNHYTQKSLSLSPG (SEQ ID NO: 19) |
| GAGGAGGAGCTGCAGGTGATTCAGCCTGACAAGTCCGTATCAGTTGCAGCTGGAGAGTCGGCCATTCTGCACT<br>GCACTGTGACCTCCCTGATCCCTGTGGGGCCCATCCAGTGGTTCAGAGGAGCTGGACCAGCCCGGGAATTAAT<br>CTACAATCAAAAGAAGGCCACTTCCCCCGGGTAACAACTGTTTCAGAGTCCACAAAGAGAGAAAACATGGAC<br>TTTTCCATCAGCATCAGTGCCATCACCCCAGCAGATGCCGGCACCTACTACTGTGTGAAGTTCCGGAAAGGGA<br>GCCCTGACACGGAGTTTAAGTCTGGAGCAGGCACTGAGCTGTCTGTGCGTGCCAAACCCTCTGCCCCCGTGGT<br>ATCGGGCCCTGCGGCGAGGGCCACACCTCAGCACGAGCCCAAATCTTGTGACAAAACTCACACATGCCCACCG<br>TGCCCAGCACCTGAACTCCTGGGGGGACCGTCAGTCTTCCTCTTCCCCCCAAAACCCAAGGACACCCTCATGA<br>TCTCCCGGACCCCTGAGGTCACATGCGTGGTGGTGGACGTGAGCCACGAAGACCCTGAGGTCAAGTTCAACTG<br>GTACGTGGACGGCGTGGAGGTGCATAATGCCAAGACAAAGCCGCGGGAGGAGCAGTACAACAGCACGTACCGT<br>GTGGTCAGCGTCCTCACCGTCCTGCACCAGGACTGGCTGAATGGCAAGGAGTACAAGTGCAAGGTCTCCAACA<br>AAGCCCTCCCAGCCCCCATCGAGAAAACCATCTCCAAAGCCAAAGGGCAGCCCCGAGAACCACAGGTGTACAC<br>CCTGCCCCCATCCCGGGATGAGCTGACCAAGAACCAGGTCAGCCTGACCTGCCTGGTCAAAGGCTTCTATCCC<br>AGCGACATCGCCGTGGAGTGGGAGAGCAATGGGCAGCCGGAGAACAACTACAAGACCACGCCTCCCGTGCTGG<br>ACTCCGACGGCTCCTTCTTCCTCTACAGCAAGCTCACCGTGGACAAGAGCAGGTGGCAGCAGGGGAACGTCTT<br>CTCATGCTCCGTGATGCATGAGGCTCTGCACAACCACTACACGCAGAAGAGCCTCTCCCTGTCTCCGGGTTGA (SEQ ID NO: 20) |
| Nucleotides coding for murine IgG1 heavy chain signal peptide<br>ATGGGATGGTCATGTATCATCCTTTTTCTGGTAGCAACTGCAACTGGAGTACATTCA (SEQ ID NO: 21) |
| Kozak<br>GCCGCCACC (SEQ ID NO: 22) |

While the application has been described above in connection with one or more embodiments, it should be understood that the application is not limited to those embodiments, and the description is intended to cover all alternatives, modifications, and equivalents, as may be included within the spirit and scope of the appended claims. All referenced cited herein are further incorporated by reference in their entirety.

REFERENCES

1. Toubai, T., et al., Siglec-G-CD24 axis controls the severity of graft-versus-host disease in mice. Blood, 2014. 123 (22): p. 3512-23
2. Shim H. Bispecific Antibodies and Antibody-Drug Conjugates for Cancer Therapy: Technological Considerations. Biomolecules. 2020 Feb. 26; 10(3):360.
3. Fairbridge, N. A., et al., Loss of CD24 in Mice Leads to Metabolic Dysfunctions and a Reduction in White Adipocyte Tissue. PLoS One, 2015. 10 (11): p. e0141966.
4. El-Mokhtar, M. A., et al., Altered Regulatory B Cell Subsets in Children with Type 1 Diabetes Mellitus. J Immunol Res, 2020. 2020: p. 8935694.
5. Tan, Y., et al., CD24: from a Hematopoietic Differentiation Antigen to a Genetic Risk Factor for Multiple Autoimmune Diseases. Clin Rev Allergy Immunol, 2016. 50 (1): p. 70-83.
6. Chen, G. Y., et al., Amelioration of sepsis by inhibiting sialidase-mediated disruption of the CD24-SiglecG interaction. Nat Biotechnol, 2011. 29 (5): p. 428-35.
7. Graft Versus Host Disease (GVHD): https://clinicaltrials.gov/ct2/show/NCT04095858?term=CD24&draw=2&rank=9
8. Antiretroviral therapy induced increase of LDL, HbA1c, hepatic steatosis and fibrosis, and other markers of inflammation: https://clinicaltrials.gov/ct2/show/NCT03960541?term=CD24&draw=2&rank=2
9. Metabolic Associated Fatty Liver Disease: https://clinicaltrials.gov/ct2/show/NCT04720560?term=CD24&draw=4&rank=23
10. Type 1 Diabetes: https://clinicaltrials.gov/ct2/show/NCT02801942?term=CD24&draw=4&rank=25
11. Type 2 Diabetes Mellitus and Cardiovascular Diseases: https://clinicaltrials.gov/ct2/show/NCT02694575?term=CD24&draw=5&rank=34
12. Rheumatoid Arthritis: https://clinicaltrials.gov/ct2/show/NCT03793270?term=CD24&draw=4&rank=24
13. Systemic Lupus Erythematosus: https://clinicaltrials.gov/ct2/show/NCT03178721?term=CD24&draw=5&rank=32
14. Multiple Sclerosis https://clinicaltrials.gov/ct2/show/NCT03257358?term=CD24&draw=5&rank=35
15. Sepsis: https://clinicaltrials.gov/ct2/show/NCT01995448?term=CD24&draw=5&rank=36
16. Shields R L, Namenuk A K, Hong K, Meng Y G, Rae J, Briggs J, Xie D, Lai J, Stadlen A, Li B, Fox J A, Presta L G. High Resolution Mapping of the Binding Site on Human IgG1 for FcγRI, FcγRII, FcγRIII, and FcRn and Design of IgG1 Variants with Improved Binding to the FcgR. JBC. 2001, 276:6591-6604.

17. Barkal, A. A., Brewer, R. E., Markovic, M., Kowarsky, M., Barkal, S. A., Zaro, B. W., Krishnan, V., Hatakeyama, J., Dorigo, O., Barkal, L. J., et al. (2019). CD24 signalling through macrophage Siglec-10 is a target for cancer immunotherapy. Nature 572(7769), 392-396.
18. Chan, S. H., Tsai, K. W., Chiu, S. Y., Kuo, W. H., Chen, H. Y., Jiang, S. S., Chang, K. J., Hung, W. C., and Wang, L. H. (2019). Identification of the Novel Role of CD24 as an Oncogenesis Regulator and Therapeutic Target for Triple-Negative Breast Cancer. Mol Cancer Ther 18(1), 147-161.
19. Friederichs J, Zeller Y, Hafezi-Moghadam A, Grone H J, Ley K, Altevogt P. The CD24/P-selectin binding pathway initiates lung arrest of human A125 adenocarcinoma cells. Cancer Res. 2000; 60: 6714-6722.
20. Wang S, Chen K, Lei Q, Ma P, Yuan A Q, Zhao Y, Jiang Y, Fang H, Xing S, Fang Y, Jiang N, Miao H, Zhang M, Sun S, Yu Z, Tao W, Zhu Q, Nie Y, Li N. The state of the art of bispecific antibodies for treating human malignancies. EMBO Mol Med. 2021 Aug. 24:e14291. doi: 10.15252/emmm 202114291.
21. Yin, S. S., and Gao, F. H. (2020). Molecular Mechanism of Tumor Cell Immune Escape Mediated by CD24/Siglec-10. Front Immunol 11, 1324.
22. Gardai S J, McPhillips K A, Frasch S C, Janssen W J, Starefeldt A, Murphy-Ullrich J E, Bratton D L, Oldenborg P A, Michalak M, Henson P M. Cell-surface calreticulin initiates clearance of viable or apoptotic cells through trans-activation of LRP on the phagocyte. Cell. 2005; 123:321-334.
23. Gennaro, ed., Remington: The Science and Practice of Pharmacy, 20th Ed., Lippincott Williams & Wilkins 2003.
24. Liu, C., Zheng, S., Shen, H., Xu, K., Chen, J., Li, H., Xu, Y., Xu, A., Chen, B., Kaku, H., et al. (2013). Clinical significance of CD24 as a predictor of bladder cancer recurrence. Oncol Lett 6(1), 96-100.
25. Nakamura et al. CD24 expression is a marker for predicting clinical outcome and regulates the epithelial-mesenchymal transition in ovarian cancer via both the Akt and ERK pathways. Oncol Rep. 2017 June; 37(6):3189-3200.
26. Obeid M, Panaretakis T, Joza N, Tufi R, Tesniere A, van Endert P, Zitvogel L, Kroemer G. Calreticulin exposure is required for the immunogenicity of gamma-irradiation and UVC lightinduced apoptosis. Cell Death Differ. 2007, 14:1848-1850.
27. Orr A W, Pedraza C E, Pallero M A, Elzie C A, Goicoechea S, Strickland D K, Murphy-Ullrich J E. Low density lipoprotein receptor-related protein is a calreticulin coreceptor that signals focal adhesion disassembly. J Cell Biol. 2003, 161:1179-1189.
28. Overdevest, J. B., Thomas, S., Kristiansen, G., Hansel, D. E., Smith, S. C., and Theodorescu, D. (2011). CD24 offers a therapeutic target for control of bladder cancer metastasis based on a requirement for lung colonization. Cancer Res 71(11), 3802-11.

The invention claimed is:

1. An isolated monoclonal antibody or an antigen binding portion thereof, that binds CD24, comprising
   i) a heavy chain variable region, wherein the heavy chain variable region comprises a heavy chain variable region CDR-1 (HV-CDR1), a HV-CDR2, and a HV-CDR3 comprising the amino acid sequences set forth in SEQ ID NOs: 1, 2, and 3, respectively; and
   ii) a light chain variable region, wherein the light chain variable region comprises a light chain variable region (CDR-1) (LV-CDR1), a LV-CDR2, and a LV-CDR3 comprising the amino acid sequences set forth in SEQ ID NOs: 4, 5, and 6, respectively.

2. The isolated monoclonal antibody or antigen binding portion thereof of claim 1, wherein the heavy chain variable region comprises an amino acid sequences having at least 90% or 95% identity to SEQ ID NOs: 7 or 10.

3. The isolated monoclonal antibody or antigen binding portion thereof of claim 1, wherein the light chain variable region comprises an amino acid sequences having at least 90% or 95% identity to SEQ ID NOs: 8, 9, or 11.

4. The isolated monoclonal antibody or antigen binding portion thereof of claim 2, wherein the heavy chain variable region and the light chain variable region comprise amino acid sequences having a least 90% or 95% identity to i) SEQ ID NOs: 7 and 8, respectively; ii) SEQ ID NOs: 7 and 9, respectively, and iii) SEQ ID NOs: 10 and 11, respectively.

5. The isolated monoclonal antibody or antigen binding portion thereof of claim 1, which is an IgG1, IgG2, or IgG4 isotype.

6. The isolated monoclonal antibody or antigen binding portion thereof of claim 1, comprising a heavy chain constant region and a light chain constant region having the amino acid sequences of SEQ ID NOs: 12 and 13, respectively.

7. The isolated monoclonal antibody or antigen binding portion thereof of claim 1, which is mouse, chimeric or humanized.

8. A nucleic acid molecule encoding the isolated monoclonal antibody or antigen binding portion thereof of claim 1.

9. An expression vector comprising the nucleic acid molecule of claim 8.

10. A host cell comprising the expression vector of claim 9.

11. A pharmaceutical composition comprising a therapeutically effective amount of the isolated monoclonal antibody or antigen binding portion thereof of claim 1, and a pharmaceutically acceptable carrier.

12. A method for treating a cancer associated with higher than physiologically normal CD24 expression in a subject in need thereof, comprising administering to the subject the pharmaceutical composition of claim 11, wherein the cancer is a solid cancer or a hematological cancer.

13. A method for treating a cancer associated with higher than physiologically normal CD24 expression in a subject in need thereof, comprising administering to the subject the pharmaceutical composition of claim 11, wherein the cancer is ovarian cancer, breast cancer, cervical cancer, endometrial cancer, acute lymphoblastic leukemia (ALL), cholangiocarcinoma, pancreatic adenocarcinoma, lung cancer, bladder cancer, pancreatic cancer, gastric adenocarcinoma, glioblastoma, or colon cancer.

14. A method for treating a cancer associated with CD24 overexpression in a subject in need thereof, comprising administering to the subject the pharmaceutical composition of claim 11.

* * * * *

SEQUENCE LISTING

```
<160> NUMBER OF SEQ ID NOS: 22

<210> SEQ ID NO 1
<211> LENGTH: 9
<212> TYPE: PRT
<213> ORGANISM: Artificial Sequence
<220> FEATURE:
<223> OTHER INFORMATION: HV-CDR-1 of IMM47C, IMM47 and IMM47H

<400> SEQUENCE: 1

Gly Tyr Ser Ile Thr Ser Gly Tyr Ser
1               5

<210> SEQ ID NO 2
<211> LENGTH: 7
<212> TYPE: PRT
<213> ORGANISM: Artificial Sequence
<220> FEATURE:
<223> OTHER INFORMATION: HV-CDR-2 of IMM47C, IMM47 and IMM47H

<400> SEQUENCE: 2

Ile His Tyr Ser Gly Ser Thr
1               5

<210> SEQ ID NO 3
<211> LENGTH: 10
<212> TYPE: PRT
<213> ORGANISM: Artificial Sequence
<220> FEATURE:
<223> OTHER INFORMATION: HV-CDR-3 of IMM47C, IMM47 and IMM47H

<400> SEQUENCE: 3

Ala Arg Gly Ala Asp Tyr Ala Leu Asp Tyr
1               5                   10

<210> SEQ ID NO 4
```

```
<211> LENGTH: 12
<212> TYPE: PRT
<213> ORGANISM: Artificial Sequence
<220> FEATURE:
<223> OTHER INFORMATION: LV-CDR-1 of IMM47C, IMM47 and IMM47H

<400> SEQUENCE: 4

Gln Ser Leu Leu Tyr Ser Ser Asn Gln Lys Asn Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: LV-CDR-2 of IMM47C, IMM47 and IMM47H

<400> SEQUENCE: 5

Trp Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: LV-CDR-3 of IMM47C, IMM47 and IMM47H

<400> SEQUENCE: 6

Gln Gln Asn Phe Ile Tyr Pro Leu Thr
1               5

<210> SEQ ID NO 7
<211> LENGTH: 117
<212> TYPE: PRT
<213> ORGANISM: Artificial Sequence
<220> FEATURE:
<223> OTHER INFORMATION: IMM47C/IMM47's heavy chain variable region

<400> SEQUENCE: 7

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
                20                  25                  30

Tyr Ser Trp His Trp Ile Arg Gln Phe Pro Gly Asn Lys Leu Glu Trp
            35                  40                  45

Met Gly Tyr Ile His Tyr Ser Gly Ser Thr Lys Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Phe Cys
                85                  90                  95

Ala Arg Gly Ala Asp Tyr Ala Leu Asp Tyr Trp Gly Gln Arg Thr Ser
            100                 105                 110

Val Thr Val Ser Ser
        115

<210> SEQ ID NO 8
<211> LENGTH: 113
<212> TYPE: PRT
<213> ORGANISM: Artificial Sequence
<220> FEATURE:
<223> OTHER INFORMATION: IMM47C's light chain variable region
```

```
<400> SEQUENCE: 8

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly His
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Asn Phe Ile Tyr Pro Leu Thr Phe Gly Ala Gly Thr Lys Leu Glu Leu
            100                 105                 110

Lys

<210> SEQ ID NO 9
<211> LENGTH: 113
<212> TYPE: PRT
<213> ORGANISM: Artificial Sequence
<220> FEATURE:
<223> OTHER INFORMATION: IMM47's light chain variable region

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Asn Phe Ile Tyr Pro Leu Thr Phe Gly Gly Gly Thr Lys Val Glu Leu
            100                 105                 110

Lys

<210> SEQ ID NO 10
<211> LENGTH: 117
<212> TYPE: PRT
<213> ORGANISM: Artificial Sequence
<220> FEATURE:
<223> OTHER INFORMATION: IMM47H's heavy chain variable region

<400> SEQUENCE: 10

Asp Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly Tyr Ile His Tyr Ser Gly Ser Thr Lys Tyr Asn Pro Ser Leu
    50                  55                  60
```

```
Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Ala Asp Tyr Ala Leu Asp Tyr Trp Gly Gln Arg Thr Ser
            100                 105                 110

Val Thr Val Ser Ser
            115

<210> SEQ ID NO 11
<211> LENGTH: 113
<212> TYPE: PRT
<213> ORGANISM: Artificial Sequence
<220> FEATURE:
<223> OTHER INFORMATION: IMM47H's light chain variable region

<400> SEQUENCE: 11

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Tyr Ser
                 20                  25                  30

Ser Asn Gln Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Asn Phe Ile Tyr Pro Leu Thr Phe Gly Gly Gly Thr Lys Val Glu Leu
            100                 105                 110

Lys

<210> SEQ ID NO 12
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 12

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Ala Ala Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 13
<211> LENGTH: 107
<212> TYPE: PRT
<213> ORGANISM: Artificial Sequence
<220> FEATURE:
<223> OTHER INFORMATION: Light chain constant region

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 1398
<212> TYPE: DNA
<213> ORGANISM: Artificial Sequence
<220> FEATURE:
<223> OTHER INFORMATION: IMM47C/IMM47's heavy chain
```

<400> SEQUENCE: 14

```
atgagagtgc tgattctttt gtgcctgttc acagcctttc ctggtatcct gtctgatgtg      60
cagcttcagg agtcaggacc tgacctggtg aaaccttctc agtcactttc actcacctgc     120
actgtcactg gctactccat caccagtggt tatagctggc actggatccg gcagtttcca     180
ggaaacaaac tggaatggat gggctacata cactatagtg gtagcactaa gtacaaccca     240
tctctcaaaa gtcgaatctc tatcactcga gacacatcca agaaccagtt cttcctgcag     300
ttgaattctg tgactactga ggacacagcc acatatttct gtgcaagagg cgcggactat     360
gctttggact actggggtca cgaacctca gtcaccgtct cctcagctag caccaagggc      420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttgggcaccc agacctacat ctgcaacgtg     660
aatcacaagc ccagcaacac caaggtggac aagagagttg agcccaaatc ttgtgacaaa     720
actcacacat gcccaccgtg cccagcacct gaactcctgg ggggaccgtc agtcttcctc     780
ttccccccaa aacccaagga caccctcatg atctcccgga cccctgaggt cacatgcgtg     840
gtggtggacg tgagccacga agaccctgag gtcaagttca actggtatgt ggacggcgtg     900
gaggtgcata atgccaagac aaagccgcgg gaggagcagt acaacgccac gtaccgtgtg     960
gtcagcgtcc tcaccgtcct gcaccagac tggctgaatg gcaaggagta caagtgcaag    1020
gtctccaaca aagccctccc agcccccatc gccgcaacca tctccaaagc caagggcag    1080
cccccgagaac cacaggtgta caccctgccc ccatcccggg aggagatgac caagaaccaa    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctattccaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gcaaatga                                                 1398
```

<210> SEQ ID NO 15
<211> LENGTH: 862
<212> TYPE: DNA
<213> ORGANISM: Artificial Sequence
<220> FEATURE:
<223> OTHER INFORMATION: IMM47C's light chain

<400> SEQUENCE: 15

```
atggattcac aggcccaggt tcttatgtta ctgctgctat gggtatctgg tacctgtggg      60
gacattgtga tgtcacagtc tccatcctcc ctagctgtgt cagttggaga gaaggttact     120
atgagctgca agtccagtca gagccttta tatagtagca tcaaaagaa ctacttggcc       180
tggtaccagc agaaaccagg gcactctcct aaactgctga tttactgggc atccactagg     240
gaatctgggg tccctgatcg cttcacaggc agtggatctg gacagatttt cactctcacc     300
atcagcagtg tgaaggctga agaccctgca gtttattact gtcagcaaaa ttttatctat     360
ccgctcacgt tcggtgctgg gaccaagctg gagctgaaac gtgagttcta gaggatccat     420
ctgggataag catgctgttt tctgtctgtc cctaacatgc cctgtgatta ccgcaaaca     480
acacacccaa gggcagaact tgttacttaa acaccatctg tttgcttc tttcctcagg       540
aactgtggct gcaccatctg tcttcatctt cccgccatct gatgagcagt tgaaatctgg     600
```

```
aactgcctct gttgtgtgcc tgctgaataa cttctatccc agagaggcca aagtacagtg    660
gaaggtggat aacgccctcc aatcgggtaa ctcccaggag agtgtcacag agcaggacag    720
caaggacagc acctacagcc tcagcagcac cctgacgctg agcaaagcag actacgagaa    780
acacaaagtc tacgcctgcg aagtcaccca tcagggcctg agctcgcccg tcacaaagag    840
cttcaacagg ggagagtgtt ag                                             862
```

<210> SEQ ID NO 16
<211> LENGTH: 859
<212> TYPE: DNA
<213> ORGANISM: Artificial Sequence
<220> FEATURE:
<223> OTHER INFORMATION: IMM47's light chain

<400> SEQUENCE: 16

```
atgggatggt catgtatcat cctttttctg gtagcaactg caactggagt acattcagac     60
attcagatga cacagagccc tagcagcctg agcgcctccg tgggcgacag agtgaccatc    120
acctgcaaga gcagccaaag cctgctgtac agcagcaatc agaagaacta cctggcctgg    180
tatcagcaga agcctggcaa ggcccctaag ctgctgatct actgggcctc acaagagag    240 agcggcgtgc ctagcagatt cagcggcagc ggcagcggca ccgacttcac cctgaccatc    300
agcagcctgc agcctgagga cttcgccacc tactactgtc agcagaactt catctaccct    360
ctgaccttcg gcggaggcac caaggtggag ctgaagcgtg agttctagag gatccatctg    420
ggataagcat gctgttttct gtctgtccct aacatgccct gtgattatcc gcaaacaaca    480
cacccaaggg cagaactttg ttacttaaac accatcctgt ttgcttcttt cctcaggaac    540
tgtggctgca ccatctgtct tcatcttccc gccatctgat gagcagttga atctggaac    600 tgcctctgtt gtgtgcctgc tgaataactt ctatcccaga gaggccaaag tacagtggaa    660
ggtggataac gccctccaat cgggtaactc ccaggagagt gtcacagagc aggacagcaa    720
ggacagcacc tacagcctca gcagcaccct gacgctgagc aaagcagact acgagaaaca    780
caaagtctac gcctgcgaag tcacccatca gggcctgagc tcgcccgtca caaagagctt    840
caacagggga gagtgttag                                                 859
```

<210> SEQ ID NO 17
<211> LENGTH: 1401
<212> TYPE: DNA
<213> ORGANISM: Artificial Sequence
<220> FEATURE:
<223> OTHER INFORMATION: IMM47H's heavy chain

<400> SEQUENCE: 17

```
atgggatggt catgtatcat cctttttctg gtagcaactg caactggagt acattcagac     60
gtgcagctgc aagagagcgg ccctggcctg gtgaagccta gcgagaccct gagcctgacc    120
tgcaccgtgt ccggctacag catcacaagc ggctacagct ggcactggat cagacagcct    180
cctggcaagg gcctggagtg gatcggctac atccactaca gcggcagcac caagtacaac    240
cctagcctga gagcagagt gaccatcagc gtggacacaa gcaagaatca gttcagcctg    300
aagctgagca gcgtgaccgc cgccgacacc gccgtgtact actgcgctag aggcgccgac    360
tacgccctgg actactgggg acagagaaca agcgtgaccg tgagcagcgc tagcaccaag    420
ggcccatcgg tcttccccct ggcaccctcc tccaagagca cctctggggg cacagcggcc    480
ctgggctgcc tggtcaagga ctacttcccc gaaccggtga cggtgtcgtg gaactcaggc    540
```

```
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta tgtggacggc    900
gtggaggtgc ataatgccaa gacaaagccg cgggaggagc agtacaacgc cacgtaccgt    960
gtggtcagcg tcctcaccgt cctgcaccaa gactggctga atggcaagga gtacaagtgc   1020
aaggtctcca acaaagccct cccagccccc atcgccgcaa ccatctccaa agccaaaggg   1080
cagccccgag aaccacaggt gtacaccctg cccccatccc gggaggagat gaccaagaac   1140
caagtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctattc caagctcacc gtggacaaga gcaggtggca gcaggggaac   1320
gtcttctcat gctccgtgat gcatgaggct ctgcacaacc actacacgca gaagagcctc   1380
tccctgtctc cgggcaaatg a                                              1401

<210> SEQ ID NO 18
<211> LENGTH: 859
<212> TYPE: DNA
<213> ORGANISM: Artificial Sequence
<220> FEATURE:
<223> OTHER INFORMATION: IMM47H's light chain

<400> SEQUENCE: 18
atgggatggt catgtatcat cctttttctg gtagcaactg caactggagt acattcagac     60
atcgtgatga cacagagccc tgacagcctg gccgtgagcc tgggcgagag agccaccatc    120
aactgcaaga gctctcagag cctgctgtac agcagcaatc agaagaacta cctggcctgg    180
tatcagcaga agcctggaca gcctcctaag ctgctgatct actgggcaag cacaagagag    240
agcggcgtgc ctgacagatt cagcggcagc ggcagcggca ccgacttcac cctgaccatc    300
agcagcctgc aagccgagga cgtggccgtg tactactgtc agcagaactt catctaccct    360
ctgaccttcg gcggcggcac caaggtggag ctgaagcgtg agttctagag gatccatctg    420
ggataagcat gctgttttct gtctgtccct aacatgccct gtgattatcc gcaaacaaca    480
cacccaaggg cagaactttg ttacttaaac accatcctgt ttgcttcttt cctcaggaac    540
tgtggctgca ccatctgtct tcatcttccc gccatctgat gagcagttga aatctggaac    600
tgcctctgtt gtgtgcctgc tgaataactt ctatcccaga gaggccaaag tacagtggaa    660
ggtggataac gccctccaat cgggtaactc ccaggagagt gtcacagagc aggacagcaa    720
ggacagcacc tacagcctca gcagcaccct gacgctgagc aaagcagact acgagaaaca    780
caaagtctac gcctgcgaag tcaccccatca gggcctgagc tcgcccgtca caaagagctt    840
caacagggga gagtgttag                                                  859

<210> SEQ ID NO 19
<211> LENGTH: 364
<212> TYPE: PRT
<213> ORGANISM: Artificial Sequence
<220> FEATURE:
<223> OTHER INFORMATION: SIRPalphaD1 mutant-Fc (IMM01)

<400> SEQUENCE: 19
```

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Ala
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
        115                 120                 125

Ala Thr Pro Gln His Glu Pro Lys Ser Cys Asp Lys Thr His Thr Cys
    130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Asp Glu Leu Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly
        355                 360

<210> SEQ ID NO 20
<211> LENGTH: 1095
<212> TYPE: DNA
<213> ORGANISM: Artificial Sequence
<220> FEATURE:
<223> OTHER INFORMATION: SIRPalphaD1 mutant-Fc (IMM01)

<400> SEQUENCE: 20

-continued

```
gaggaggagc tgcaggtgat tcagcctgac aagtccgtat cagttgcagc tggagagtcg        60
gccattctgc actgcactgt gacctccctg atccctgtgg ggcccatcca gtggttcaga       120
ggagctggac cagcccggga attaatctac aatcaaaaag aaggccactt cccccgggta       180
acaactgttt cagagtccac aaagagagaa aacatggact tttccatcag catcagtgcc       240
atcaccccag cagatgccgg cacctactac tgtgtgaagt tccggaaagg gagccctgac       300
acggagttta agtctggagc aggcactgag ctgtctgtgc gtgccaaacc ctctgccccc       360
gtggtatcgg gccctgcggc gagggccaca cctcagcacg agcccaaatc ttgtgacaaa       420
actcacacat gcccaccgtg cccagcacct gaactcctgg gggaccgtc agtcttcctc        480 ttccccccaa acccaagga caccctcatg atctcccgga cccctgaggt cacatgcgtg        540
gtggtggacg tgagccacga agaccctgag gtcaagttca actggtacgt ggacggcgtg       600
gaggtgcata atgccaagac aaagccgcgg gaggagcagt acaacagcac gtaccgtgtg       660
gtcagcgtcc tcaccgtcct gcaccaggac tggctgaatg gcaaggagta caagtgcaag       720
gtctccaaca aagccctccc agcccccatc gagaaaacca tctccaaagc caaagggcag       780
ccccgagaac cacaggtgta caccctgccc ccatcccggg atgagctgac caagaaccag       840
gtcagcctga cctgcctggt caaaggcttc tatcccagcg acatcgccgt ggagtgggag       900
agcaatgggc agccggagaa caactacaag accacgcctc ccgtgctgga ctccgacggc       960
tccttcttcc tctacagcaa gctcaccgtg gacaagagca ggtggcagca ggggaacgtc      1020
ttctcatgct ccgtgatgca tgaggctctg cacaaccact acacgcagaa gagcctctcc      1080
ctgtctccgg gttga                                                       1095
```

<210> SEQ ID NO 21
<211> LENGTH: 57
<212> TYPE: DNA
<213> ORGANISM: Artificial Sequence
<220> FEATURE:
<223> OTHER INFORMATION: Nucleotides coding for murine IgG1 heavy chain
      signal peptide

<400> SEQUENCE: 21

```
atgggatggt catgtatcat ccttttcctg gtagcaactg caactggagt acattca            57
```

<210> SEQ ID NO 22
<211> LENGTH: 9
<212> TYPE: DNA
<213> ORGANISM: Artificial Sequence
<220> FEATURE:
<223> OTHER INFORMATION: Kozak

<400> SEQUENCE: 22

```
gccgccacc                                                                  9
```